(12) United States Patent
Fredrickson et al.

(10) Patent No.: US 12,157,238 B2
(45) Date of Patent: *Dec. 3, 2024

(54) SYSTEMS AND METHODS FOR ROBOTIC ARM ALIGNMENT AND DOCKING

(71) Applicant: Auris Health, Inc., Redwood City, CA (US)

(72) Inventors: Benjamin Robert Fredrickson, Belmont, CA (US); Travis C. Covington, Campbell, CA (US); Jason Tomas Wilson, Redwood City, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/467,517

(22) Filed: Sep. 14, 2023

(65) Prior Publication Data
US 2024/0001560 A1 Jan. 4, 2024

Related U.S. Application Data

(63) Continuation of application No. 17/676,117, filed on Feb. 18, 2022, now Pat. No. 11,801,605, which is a
(Continued)

(51) Int. Cl.
*B25J 19/02* (2006.01)
*B25J 9/00* (2006.01)
(Continued)

(52) U.S. Cl.
CPC .......... *B25J 9/1697* (2013.01); *B25J 9/0084* (2013.01); *B25J 9/1682* (2013.01); *B25J 19/023* (2013.01);
(Continued)

(58) Field of Classification Search
CPC ..... A61B 34/30; A61B 34/20; A61B 17/3421; A61B 2034/2065; A61B 2017/00477;
(Continued)

(56) References Cited

U.S. PATENT DOCUMENTS 5,199,417 A 4/1993 Muller
5,876,325 A 3/1999 Mizuno
(Continued)

FOREIGN PATENT DOCUMENTS

EP 0347098 A2 12/1989
WO 2015142933 A1 9/2015
(Continued)

OTHER PUBLICATIONS

Ishak et al., Design and Implementation of Robot Assisted Surgery Based on Internet of Things (IoT), 2018, IEEE, p. 65-70 (Year: 2018).*
(Continued)

*Primary Examiner* — McDieunel Marc
(74) *Attorney, Agent, or Firm* — Frost Brown Todd LLP

(57) ABSTRACT

Certain aspects relate to systems and techniques for preparing a robotic system for surgery. In one aspect, the method includes a robotic arm, a sensor configured to generate information indicative of a location of the robotic arm, a processor, and at least one computer-readable memory in communication with the processor and having stored thereon computer-executable instructions. The instructions are configured to cause the processor to receive the information from the sensor, determine that the robotic arm is located at a first position in which a first axis associated with the robotic arm is not in alignment with a second axis associated with a port installed in a patient, and provide a command to move the robotic arm to a second position in
(Continued)

which the first axis associated with the robotic arm is in alignment with the second axis.

20 Claims, 30 Drawing Sheets

Related U.S. Application Data continuation of application No. 16/584,624, filed on Sep. 26, 2019, now Pat. No. 11,254,009.

(60) Provisional application No. 62/783,089, filed on Dec. 20, 2018.

(51) Int. Cl.
  *B25J 9/16* (2006.01)
  *B25J 19/04* (2006.01)

(52) U.S. Cl.
  CPC .......... *B25J 19/026* (2013.01); *B25J 19/027* (2013.01); *B25J 19/04* (2013.01)

(58) Field of Classification Search
  CPC .......... A61B 46/10; A61B 2034/2055; A61B 2034/301; A61B 2090/571; A61B 2090/3937; B25J 9/0084; B25J 9/1697; B25J 19/023; B25J 19/026; B25J 9/1682; B25J 19/04; B25J 19/027
  See application file for complete search history.

(56) References Cited

U.S. PATENT DOCUMENTS

| | | | |
|---|---|---|---|
| 7,155,316 | B2 | 12/2006 | Sutherland et al. |
| 8,021,326 | B2 | 9/2011 | Moll |
| 8,652,030 | B2 | 2/2014 | Matsuura |
| 9,108,318 | B2 | 8/2015 | Diolaiti |
| 9,504,604 | B2 | 11/2016 | Alvarez |
| 9,561,083 | B2 | 2/2017 | Yu |
| 9,622,827 | B2 | 4/2017 | Yu |
| 9,636,184 | B2 | 5/2017 | Lee |
| 9,668,768 | B2 | 6/2017 | Piron |
| 9,713,509 | B2 | 7/2017 | Schuh |
| 9,717,563 | B2 | 8/2017 | Tognaccini |
| 9,727,963 | B2 | 8/2017 | Mintz |
| 9,737,371 | B2 | 8/2017 | Romo |
| 9,737,373 | B2 | 8/2017 | Schuh |
| 9,744,335 | B2 | 8/2017 | Jiang |
| 9,763,741 | B2 | 9/2017 | Alvarez |
| 9,782,229 | B2 | 10/2017 | Crawford |
| 9,788,910 | B2 | 10/2017 | Schuh |
| 9,827,054 | B2 | 11/2017 | Richmond |
| 9,844,412 | B2 | 12/2017 | Bogusky |
| 9,867,635 | B2 | 1/2018 | Alvarez |
| 9,872,737 | B2 | 1/2018 | Nixon |
| 9,918,681 | B2 | 3/2018 | Wallace |
| 9,931,025 | B1 | 4/2018 | Graetzel |
| 9,949,749 | B2 | 4/2018 | Noonan |
| 9,949,799 | B2 | 4/2018 | Hingwe |
| 9,955,986 | B2 | 5/2018 | Shah |
| 9,962,228 | B2 | 5/2018 | Schuh |
| 9,980,785 | B2 | 5/2018 | Schuh |
| 9,993,313 | B2 | 6/2018 | Schuh |
| 10,016,900 | B1 | 7/2018 | Meyer |
| 10,022,192 | B1 | 7/2018 | Ummalaneni |
| 10,080,576 | B2 | 9/2018 | Romo |
| 10,136,959 | B2 | 11/2018 | Mintz |
| 10,145,747 | B1 | 12/2018 | Lin |
| 10,149,720 | B2 | 12/2018 | Romo |
| 10,154,822 | B2 | 12/2018 | Henderson |
| 10,159,532 | B1 | 12/2018 | Ummalaneni |
| 10,159,533 | B2 | 12/2018 | Moll |
| 10,169,875 | B2 | 1/2019 | Mintz |
| 10,172,687 | B2 | 1/2019 | Garbus |
| 10,219,874 | B2 | 3/2019 | Yu |
| 10,231,793 | B2 | 3/2019 | Romo |
| 10,231,867 | B2 | 3/2019 | Alvarez |
| 10,244,926 | B2 | 4/2019 | Noonan |
| 10,285,574 | B2 | 5/2019 | Landey |
| 10,299,870 | B2 | 5/2019 | Connolly |
| 10,307,220 | B2 | 6/2019 | Piferi et al. |
| 10,314,463 | B2 | 6/2019 | Agrawal |
| 10,327,862 | B2 | 6/2019 | Lubinski |
| 10,383,765 | B2 | 8/2019 | Alvarez |
| 10,398,518 | B2 | 9/2019 | Yu |
| 10,405,939 | B2 | 9/2019 | Romo |
| 10,405,940 | B2 | 9/2019 | Romo |
| 10,426,559 | B2 | 10/2019 | Graetzel |
| 10,426,661 | B2 | 10/2019 | Kintz |
| 10,434,660 | B2 | 10/2019 | Meyer |
| 10,464,209 | B2 | 11/2019 | Ho |
| 10,470,830 | B2 | 11/2019 | Hill |
| 10,482,599 | B2 | 11/2019 | Mintz |
| 10,493,241 | B2 | 12/2019 | Jiang |
| 10,500,001 | B2 | 12/2019 | Yu |
| 10,517,692 | B2 | 12/2019 | Eyre |
| 10,524,866 | B2 | 1/2020 | Srinivasan |
| 10,539,478 | B2 | 1/2020 | Lin |
| 10,543,048 | B2 | 1/2020 | Noonan |
| 10,555,775 | B2 | 2/2020 | Hoffman et al. |
| 10,555,778 | B2 | 2/2020 | Ummalaneni |
| 10,631,949 | B2 | 4/2020 | Schuh et al. |
| 10,639,108 | B2 | 5/2020 | Romo et al. |
| 10,639,109 | B2 | 5/2020 | Bovay et al. |
| 10,639,114 | B2 | 5/2020 | Schuh |
| 10,646,291 | B2 | 5/2020 | Turner |
| 10,667,871 | B2 | 6/2020 | Romo et al. |
| 10,667,875 | B2 | 6/2020 | DeFonzo et al. |
| 10,682,189 | B2 | 6/2020 | Schuh et al. |
| 10,702,348 | B2 | 7/2020 | Moll et al. |
| 10,716,461 | B2 | 7/2020 | Jenkins |
| 10,743,751 | B2 | 8/2020 | Landey et al. |
| 10,744,035 | B2 | 8/2020 | Alvarez et al. |
| 10,751,140 | B2 | 8/2020 | Wallace et al. |
| 10,765,487 | B2 | 9/2020 | Ho |
| 11,052,930 | B2 | 7/2021 | Schaller |
| 11,254,009 | B2 * | 2/2022 | Fredrickson ............. B25J 19/04 |
| 11,259,870 | B2 | 3/2022 | DiMaio et al. |
| 11,324,558 | B2 | 5/2022 | Graetzel |
| 11,801,605 | B2 | 10/2023 | Fredrickson |
| 2002/0082612 | A1 | 6/2002 | Moll |
| 2003/0181809 | A1 | 9/2003 | Hall |
| 2004/0176751 | A1 | 9/2004 | Weitzner |
| 2006/0058617 | A1 | 3/2006 | Sano |
| 2006/0178556 | A1 | 8/2006 | Hasser |
| 2008/0147089 | A1 | 6/2008 | Loh |
| 2009/0005768 | A1 | 1/2009 | Sharareh |
| 2009/0048611 | A1 | 2/2009 | Funda |
| 2009/0088774 | A1 | 4/2009 | Swarup |
| 2009/0326318 | A1 | 12/2009 | Tognaccini |
| 2010/0100045 | A1 | 4/2010 | Pravongviengkham |
| 2010/0234857 | A1 | 9/2010 | Itkowitz |
| 2011/0277775 | A1 | 11/2011 | Holop |
| 2012/0283747 | A1 | 11/2012 | Popovic |
| 2012/0302869 | A1 | 11/2012 | Koyrakh |
| 2014/0051049 | A1 | 2/2014 | Jarc |
| 2014/0142591 | A1 | 5/2014 | Alvarez |
| 2014/0243801 | A1 | 8/2014 | Fanelli |
| 2014/0357984 | A1 | 12/2014 | Wallace |
| 2014/0364870 | A1 | 12/2014 | Alvarez |
| 2015/0025549 | A1 | 1/2015 | Kilroy |
| 2015/0045675 | A1 | 2/2015 | Chernomorsky |
| 2015/0088161 | A1 | 3/2015 | Hata |
| 2015/0223832 | A1 | 8/2015 | Swaney |
| 2015/0297299 | A1 | 10/2015 | Yeung |
| 2015/0305650 | A1 | 10/2015 | Hunter |
| 2016/0001038 | A1 | 1/2016 | Romo |
| 2016/0030240 | A1 | 2/2016 | Gonenc et al. |
| 2016/0074131 | A1 | 3/2016 | Lubinski |
| 2016/0113728 | A1 | 4/2016 | Piron et al. |
| 2016/0270865 | A1 | 9/2016 | Landey |
| 2016/0287279 | A1 | 10/2016 | Bovay |
| 2016/0321956 | A1 | 11/2016 | Jarc et al. |

(56) References Cited

U.S. PATENT DOCUMENTS

| | | |
|---|---|---|
| 2016/0361132 A1 | 12/2016 | Piferi et al. |
| 2017/0007337 A1 | 1/2017 | Dan |
| 2017/0071456 A1 | 3/2017 | Ratnakar |
| 2017/0095299 A1 | 4/2017 | Hendrick |
| 2017/0119481 A1 | 5/2017 | Romo |
| 2017/0135710 A1 | 5/2017 | Hasegawa et al. |
| 2017/0135833 A1 | 5/2017 | Syed |
| 2017/0143442 A1 | 5/2017 | Tesar |
| 2017/0165011 A1 | 6/2017 | Bovay |
| 2017/0172674 A1 | 6/2017 | Hanuschik |
| 2017/0189118 A1 | 7/2017 | Chopra |
| 2017/0189131 A1 | 7/2017 | Weir |
| 2017/0202627 A1 | 7/2017 | Sramek |
| 2017/0209073 A1 | 7/2017 | Sramek |
| 2017/0290631 A1 | 10/2017 | Lee |
| 2017/0340396 A1 | 11/2017 | Romo |
| 2017/0367782 A1 | 12/2017 | Schuh |
| 2018/0025666 A1 | 1/2018 | Ho |
| 2018/0042680 A1 | 2/2018 | DiMaio et al. |
| 2018/0049824 A1 | 2/2018 | Harris et al. |
| 2018/0098817 A1 | 4/2018 | Nichogi |
| 2018/0214011 A1 | 8/2018 | Graetzel |
| 2018/0221038 A1 | 8/2018 | Noonan |
| 2018/0221039 A1 | 8/2018 | Shah |
| 2018/0228559 A1 | 8/2018 | Brierton |
| 2018/0250083 A1 | 9/2018 | Schuh |
| 2018/0271616 A1 | 9/2018 | Schuh |
| 2018/0279852 A1 | 10/2018 | Rafii-Tari |
| 2018/0280660 A1 | 10/2018 | Landey |
| 2018/0289431 A1 | 10/2018 | Draper |
| 2018/0325499 A1 | 11/2018 | Landey |
| 2018/0333044 A1 | 11/2018 | Jenkins |
| 2018/0338799 A1 | 11/2018 | Hladio |
| 2018/0360435 A1 | 12/2018 | Romo |
| 2018/0368920 A1 | 12/2018 | Ummalaneni |
| 2019/0000559 A1 | 1/2019 | Berman |
| 2019/0000560 A1 | 1/2019 | Berman |
| 2019/0000576 A1 | 1/2019 | Mintz |
| 2019/0083183 A1 | 3/2019 | Moll |
| 2019/0110839 A1 | 4/2019 | Rafii-Tari |
| 2019/0110843 A1 | 4/2019 | Ummalaneni |
| 2019/0151148 A1 | 5/2019 | Alvarez |
| 2019/0167366 A1 | 6/2019 | Ummalaneni |
| 2019/0175009 A1 | 6/2019 | Mintz |
| 2019/0175062 A1 | 6/2019 | Rafii-Tari |
| 2019/0175799 A1 | 6/2019 | Hsu |
| 2019/0183585 A1 | 6/2019 | Rafii-Tari |
| 2019/0183587 A1 | 6/2019 | Rafii-Tari |
| 2019/0200981 A1 | 7/2019 | Harris |
| 2019/0201111 A1 | 7/2019 | Shelton, IV |
| 2019/0201136 A1 | 7/2019 | Shelton, IV |
| 2019/0206565 A1 | 7/2019 | Shelton, IV |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz |
| 2019/0246882 A1 | 8/2019 | Graetzel |
| 2019/0262086 A1 | 8/2019 | Connolly |
| 2019/0269468 A1 | 9/2019 | Hsu |
| 2019/0274764 A1 | 9/2019 | Romo |
| 2019/0290109 A1 | 9/2019 | Agrawal |
| 2019/0298160 A1 | 10/2019 | Ummalaneni |
| 2019/0298460 A1 | 10/2019 | Al-Jadda |
| 2019/0298465 A1 | 10/2019 | Chin |
| 2019/0328213 A1 | 10/2019 | Landey |
| 2019/0336238 A1 | 11/2019 | Yu |
| 2019/0365201 A1 | 12/2019 | Noonan |
| 2019/0365209 A1 | 12/2019 | Ye |
| 2019/0365479 A1 | 12/2019 | Rafii-Tari |
| 2019/0365486 A1 | 12/2019 | Srinivasan |
| 2019/0374297 A1 | 12/2019 | Wallace |
| 2019/0375383 A1 | 12/2019 | Auer |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054408 A1 | 2/2020 | Schuh |
| 2020/0060516 A1 | 2/2020 | Baez, Jr. |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho et al. |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0198147 A1 | 6/2020 | Fredrickson |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268453 A1 | 8/2020 | Fuerst et al. |
| 2020/0268459 A1 | 8/2020 | Noonan |
| 2020/0268460 A1 | 8/2020 | Tse |
| 2020/0281787 A1 | 9/2020 | Ruiz |
| 2020/0289205 A1 | 9/2020 | Scheib |
| 2020/0289220 A1 | 9/2020 | Denlinger |
| 2020/0289221 A1 | 9/2020 | Denlinger |
| 2020/0405419 A1 | 12/2020 | Mao |
| 2021/0030501 A1 | 2/2021 | Eyre |
| 2021/0212776 A1 | 7/2021 | Schmitt |
| 2022/0406452 A1* | 12/2022 | Shelton, IV ......... H03K 17/955 |
| 2023/0146947 A1* | 5/2023 | Shelton, IV ....... A61B 17/1285 606/144 |
| 2024/0081922 A1* | 3/2024 | Leclere ................. A61B 34/30 |
| 2024/0081933 A1* | 3/2024 | Beckman ............... B25J 19/005 |

FOREIGN PATENT DOCUMENTS

| | | |
|---|---|---|
| WO | 2017048194 A1 | 3/2017 |
| WO | 2018187069 A1 | 10/2018 |

OTHER PUBLICATIONS

Kruse et al., A sensor-based dual-arm tele-robotic manipulation platform, 2013, IEEE, p. 350-355 (Year: 2013).*

Jhang et al., Multi-sensor based glove control of an industrial mobile robot arm, 2017, IEEE, p. 1-6 (Year: 2017).*

Roh et al., Development of the SAIT single-port surgical access robot slave arm based on RCM Mechanism, 2015, IEEE, p. 5285-5290 (Year: 2015).*

Carignan, Craig R., et al.; "Controlling Robots On-Orbit"; Proceedings of the 2001 IEEE International Symposium on Computational Intelligence in Robotics and Automation; Jul. 29-Aug. 1, 2001; Baniff, Alberta Canada; 6 pages.

Darwiche, Fadi, et al.; "Operative Technique and Early Experience for Robotic Assisted Laparoscopic Nephroureterectomy (RALNU) using da Vinci XI"; , SpringerPlus; 2015; 5 pages.

PCT International Search Report and PCT Written Opinion of the International Searching Authority; Application No. PCT/2019/053122; Dec. 13, 2019; 9 pages.

Ishak, Mohamad Khairi et al.; "Design and Implementation of Robot Assisted Surgery Based on Internet of Things (IoT)"; 2017 International Conference on Advanced Computing and Applications; 2017; 6 pages.

Jhang, Li-Hu et al.; "Multi-Sensor Based Glove Control of an Industrial Mobile Robot Arm"; IEEE; 2017; 6 pages.

Kofman, Jonathan et al.; "Teleoperation of a Robot Manipulator Using a Vision-Based Human-Robot Interface"; IEEE Transactions on Industrial Electronics; vol. 52, No. 5; Oct. 2005; 14 pages.

(56) References Cited

OTHER PUBLICATIONS

Kruse, Daniel et al.; "A Sensor-Based Dual-Arm Tele-Robotic Manipulation Platform"; 2013 IEEE International Conference on Automation Science and Engineering (CASE); 2013; 6 pages.

Rahimi, R., et al.; "An Industrial Robotics Application with Cloud Computing and High-Speed Networking"; 2017 First IEEE International Conference on Robotic Computing; 2017; 8 pages.

Sasaki, Kazuhito, et al.; "Laparoscopic Hemicolectomy for a Patient with Situs Inversus Totalis: A Case Report"; International Journal of Surgery Case Reports; Oct. 16, 2017; 4 pages.

Zhang, Lei, et al.; "A Teleoperation System for a Humanoid Robot with Multiple Information Feedback and Operational Modes"; 2005 IEEE International Conference on Robotics and Biomimetics; 2005; 5 pages.

Zhang, Jianweia, et al.; "A Two-Arm Situated Artificial Communicator for Human-Robot Cooperative Assembly"; IEEE Transactions on Industrial Electronics; vol. 50, No. 4; Aug. 2003; 8 pages.

Extended European Search Report; Application No. 19900133.0; Jun. 21, 2022; 10 pages.

Notice of Allowance dated Oct. 14, 2021; U.S. Appl. No. 16/584,624, filed Sep. 26, 2019; 17 pages.

Office Acton dated Jan. 12, 2023; U.S. Appl. No. 17/676,117 filed Feb. 18, 2022; 26 pages.

Notice of Allowance dated Jun. 16, 2023; U.S. Appl. No. 17/676,117 filed Feb. 18, 2022; 9 pages.

U.S. Appl. No. 18/668,883, entitled "Systems and Methods for Robotic Arm Alignment and Docking," filed May 20, 2024.

* cited by examiner

SYSTEMS AND METHODS FOR ROBOTIC ARM ALIGNMENT AND DOCKING

CROSS-REFERENCE TO RELATED APPLICATIONS

This application is a continuation of U.S. patent application Ser. No. 17/676,117 filed Feb. 18, 2022, now U.S. Pat. No. 11,801,605, issued Oct. 31, 2023, entitled, "SYSTEMS AND METHODS FOR ROBOTIC ARM ALIGNMENT AND DOCKING," which is a continuation of U.S. patent application Ser. No. 16/584,624 filed Sep. 26, 2019, now U.S. Pat. No. 11,254,009, issued Feb. 22, 2022, entitled, "SYSTEMS AND METHODS FOR ROBOTIC ARM ALIGNMENT AND DOCKING," which claims priority to U.S. Provisional Application No. 62/783,089 filed Dec. 20, 2018 entitled, "SYSTEMS AND METHODS FOR ROBOTIC ARM ALIGNMENT AND DOCKING," all of which are incorporated by reference herein in their entireties.

TECHNICAL FIELD

The disclosure herein is directed to systems and methods for the alignment and docking of robotic arm, and more particularly to computer assisted alignment and/or docking of a robotic arm with a target.

BACKGROUND

Before performing a surgical procedure, robotic arm(s) that support surgical instrument(s) may be "docked" to corresponding target(s) placed on a patient. The target may include a port such as a cannula or an access point such as a natural orifice. When the target is a port, the docking of a robotic arm to the port may include coupling or otherwise latching the robotic arm to the port. The docking process can occur before the start of any surgical procedure, or mid-procedure (e.g., occasionally, a surgeon may need to use different cannulas and re-dock one or more robotic arms). The docking process is typically performed manually and may involve a surgeon or clinician moving a robotic arm into alignment with a port to dock the robotic arm to the port. Once the docking process is completed, a surgical instrument can be inserted coaxially to the port and to gain access to an internal region of the patient.

SUMMARY

The systems, methods and devices of this disclosure each have several innovative aspects, no single one of which is solely responsible for the desirable attributes disclosed herein.

In one aspect, there is provided a system, comprising: a robotic arm; a sensor configured to generate information indicative of a location of the robotic arm; a processor; and at least one computer-readable memory in communication with the processor and having stored thereon computer-executable instructions to cause the processor to: receive the information from the sensor, determine that the robotic arm is located at a first position in which a first axis associated with the robotic arm is not in alignment with a second axis associated with a port installed in a patient, and provide a command to move the robotic arm to a second position in which the first axis associated with the robotic arm is in alignment with the second axis.

In another aspect, there is provided a method of preparing a robotic system for surgery, comprising: moving a robotic arm from a first position to a second position based on information generated by a sensor, the information indicative of a location of the robotic arm, wherein in the first position a first axis associated with the robotic arm is not in alignment with a second axis of a port placed in a patient, and wherein in the second position the first axis associated with the robotic arm is in alignment with the second axis.

In yet another aspect, there is provided a non-transitory computer readable storage medium having stored thereon instructions that, when executed, cause at least one computing device to: receive information from a sensor configured to generate information indicative of a location of a port; determine that a robotic arm is located at a first position in which a tool path axis associated with the robotic arm is not in alignment with an insertion axis of the port installed in a patient; and provide a command to move the robotic arm to a second position in which the tool path axis associated with the robotic arm is in alignment with the insertion axis.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart

Figure 1:
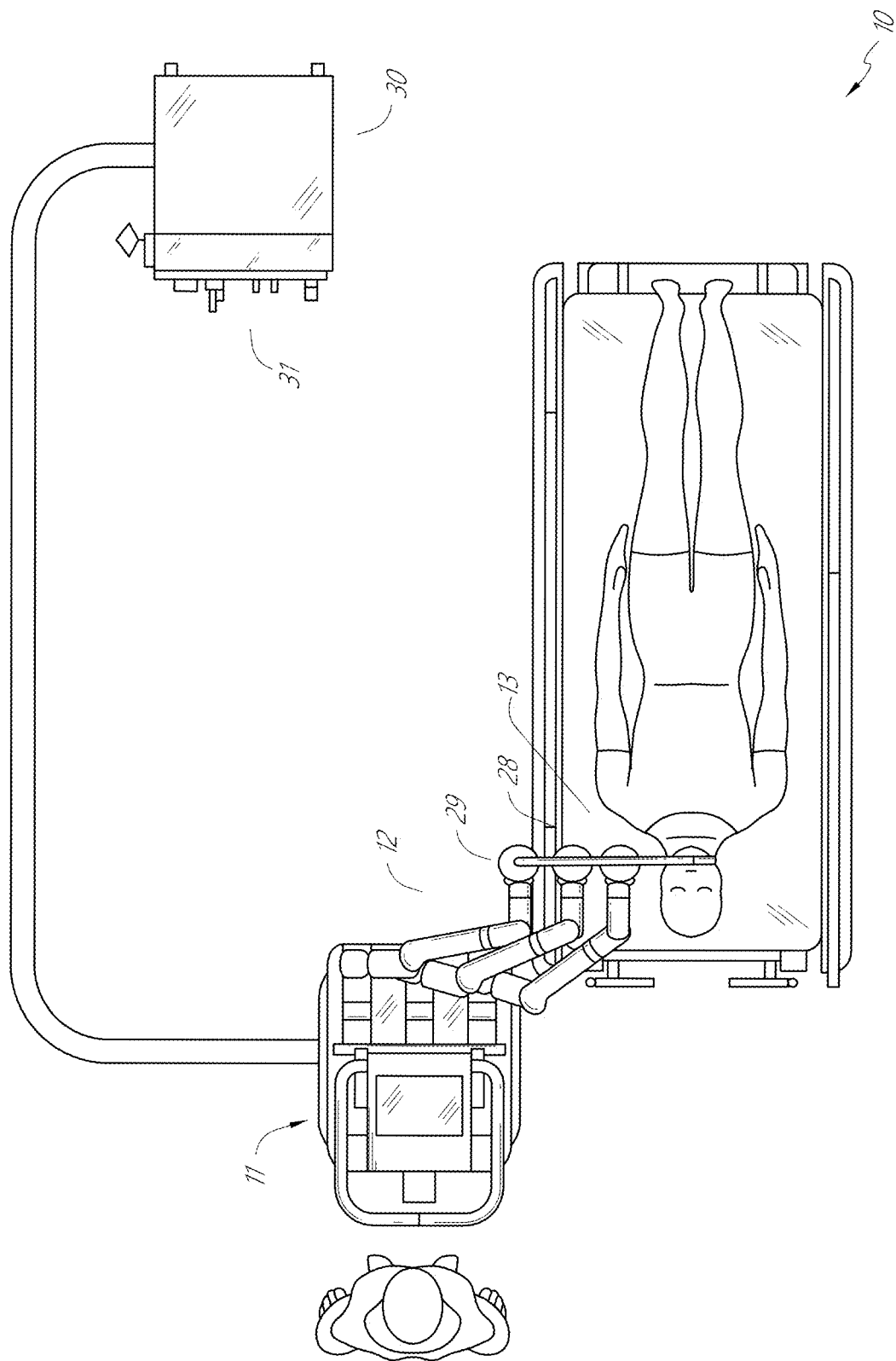
FIG. 1 illustrates an embodiment of a cart-based robotic system arranged for diagnostic and/or therapeutic bronchoscopy.
Figure 2:
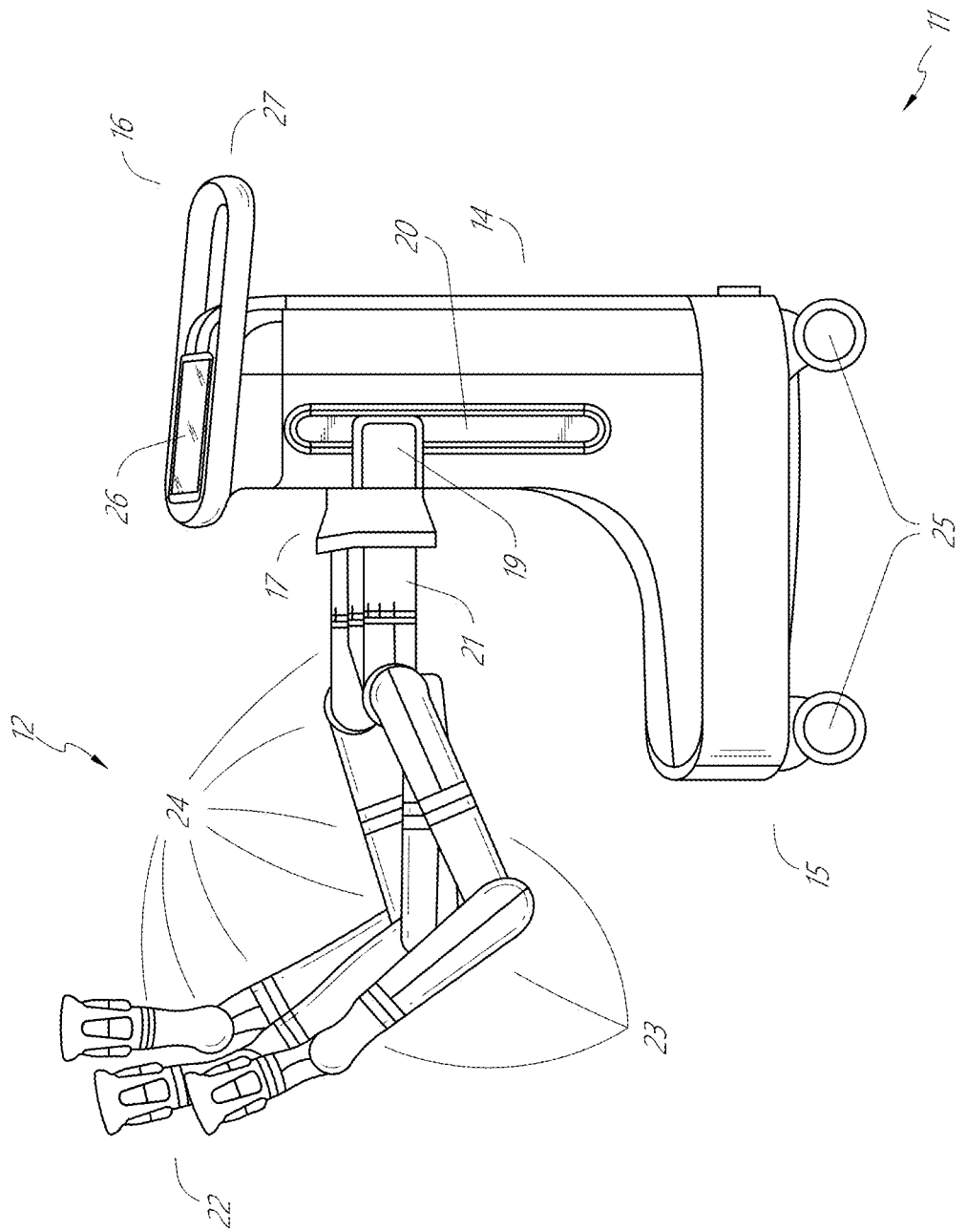
FIG. 2 depicts further aspects of the robotic system of FIG. 1.

The robotically enabled medical system may be configured in a variety of ways depending on the particular procedure. FIG. 1 illustrates an embodiment of a cart-based robotically enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool.

The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
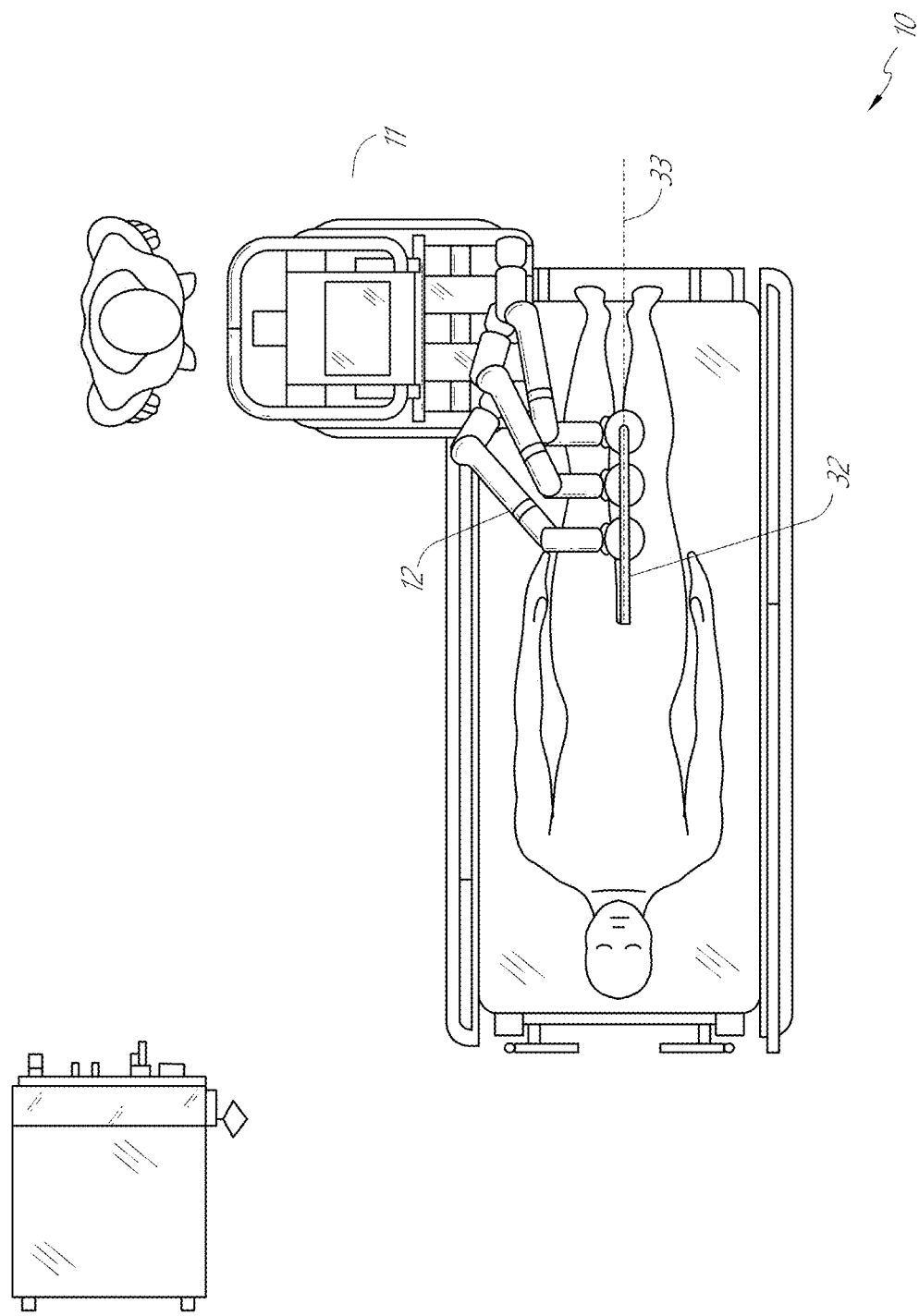
FIG. 3 illustrates an embodiment of the robotic system of FIG. 1 arranged for ureteroscopy.

FIG. 3 illustrates an embodiment of a robotically enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
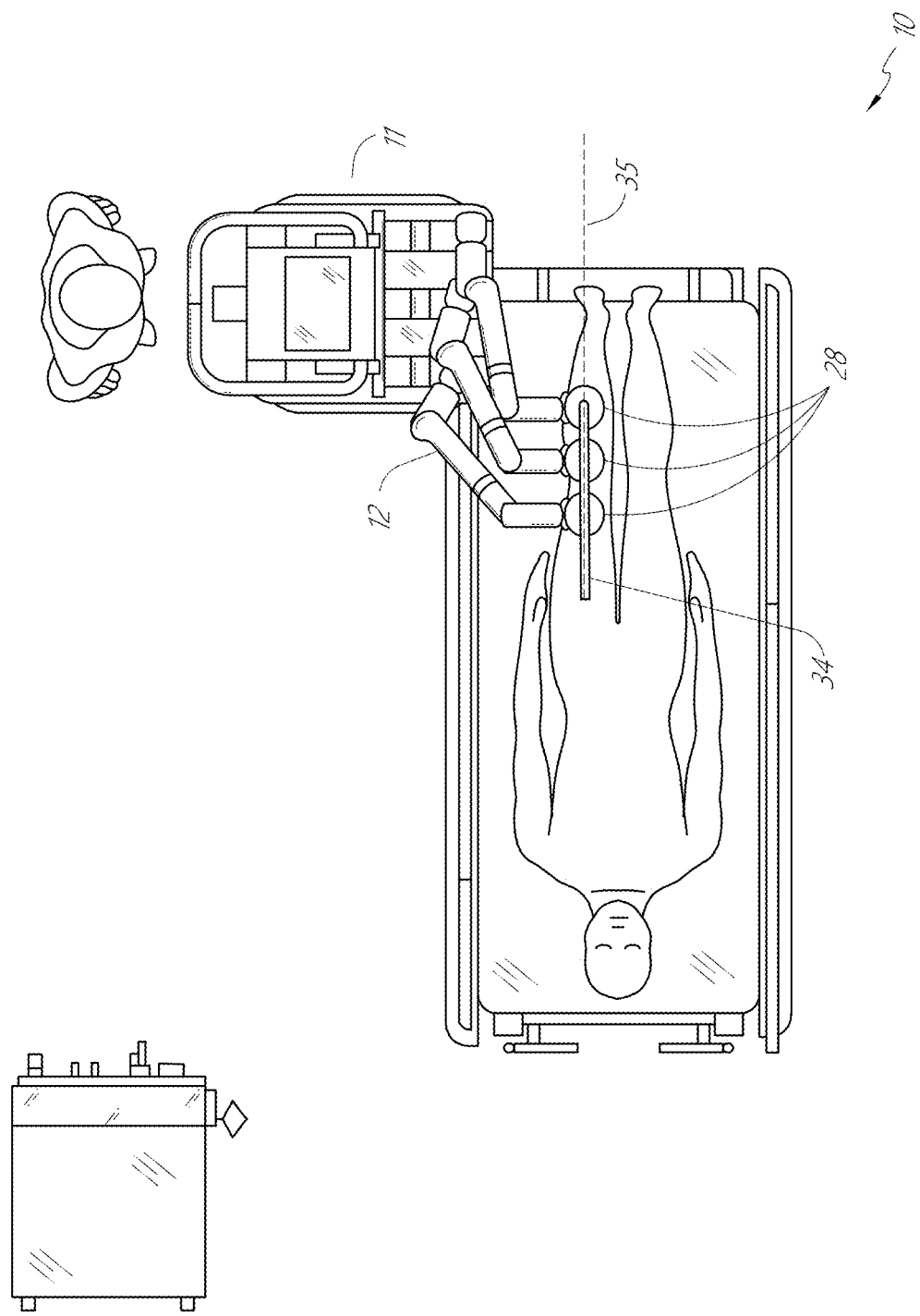
FIG. 4 illustrates an embodiment of the robotic system of FIG. 1 arranged for a vascular procedure.

FIG. 4 illustrates an embodiment of a robotically enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table

Figure 5:
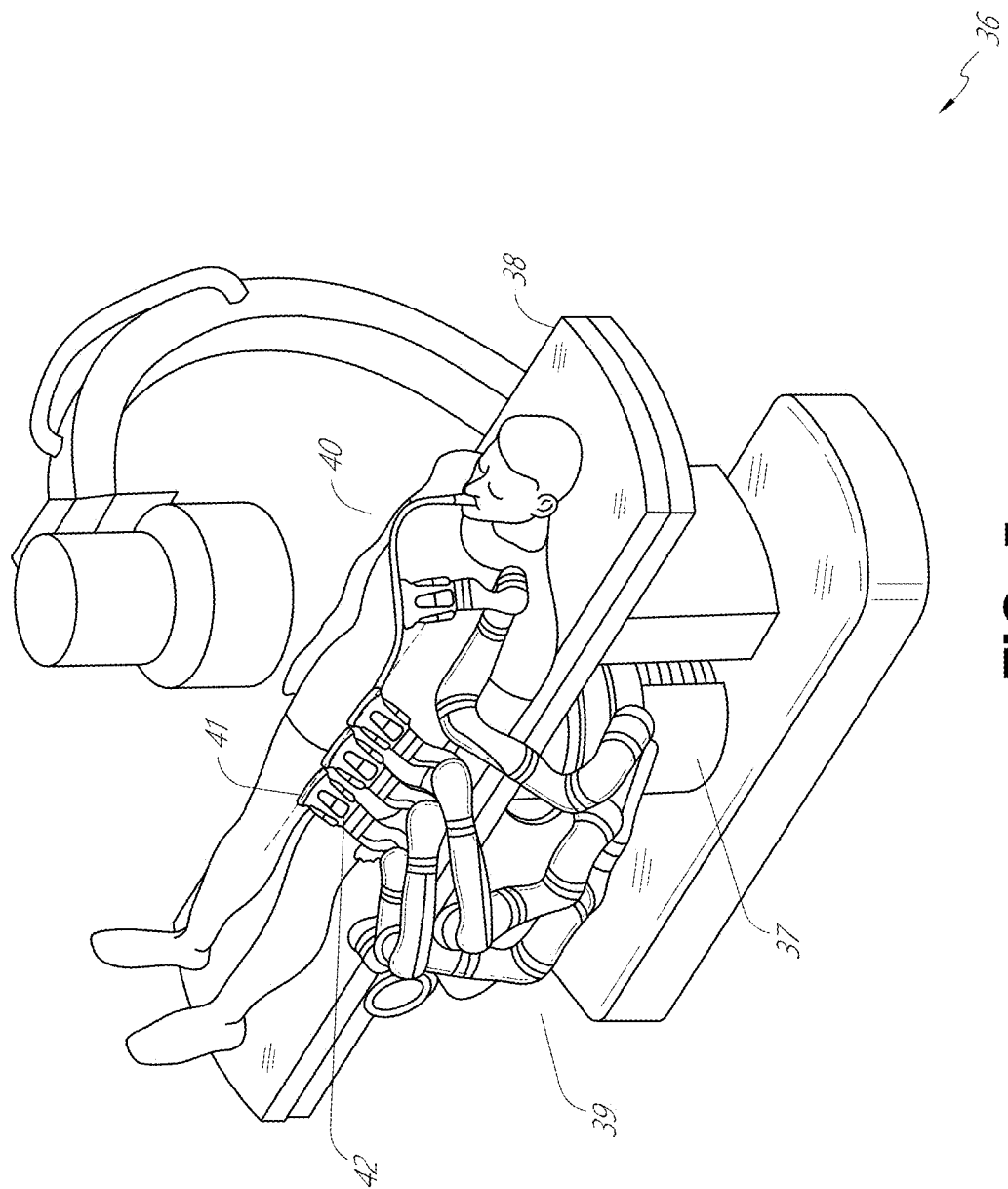
FIG. 5 illustrates an embodiment of a table-based robotic system arranged for a bronchoscopic procedure.

Embodiments of the robotically enabled medical system may also incorporate the patient's table. Incorporation of the table reduces the amount of capital equipment within the operating room by removing the cart, which allows greater access to the patient. FIG. 5 illustrates an embodiment of such a robotically enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
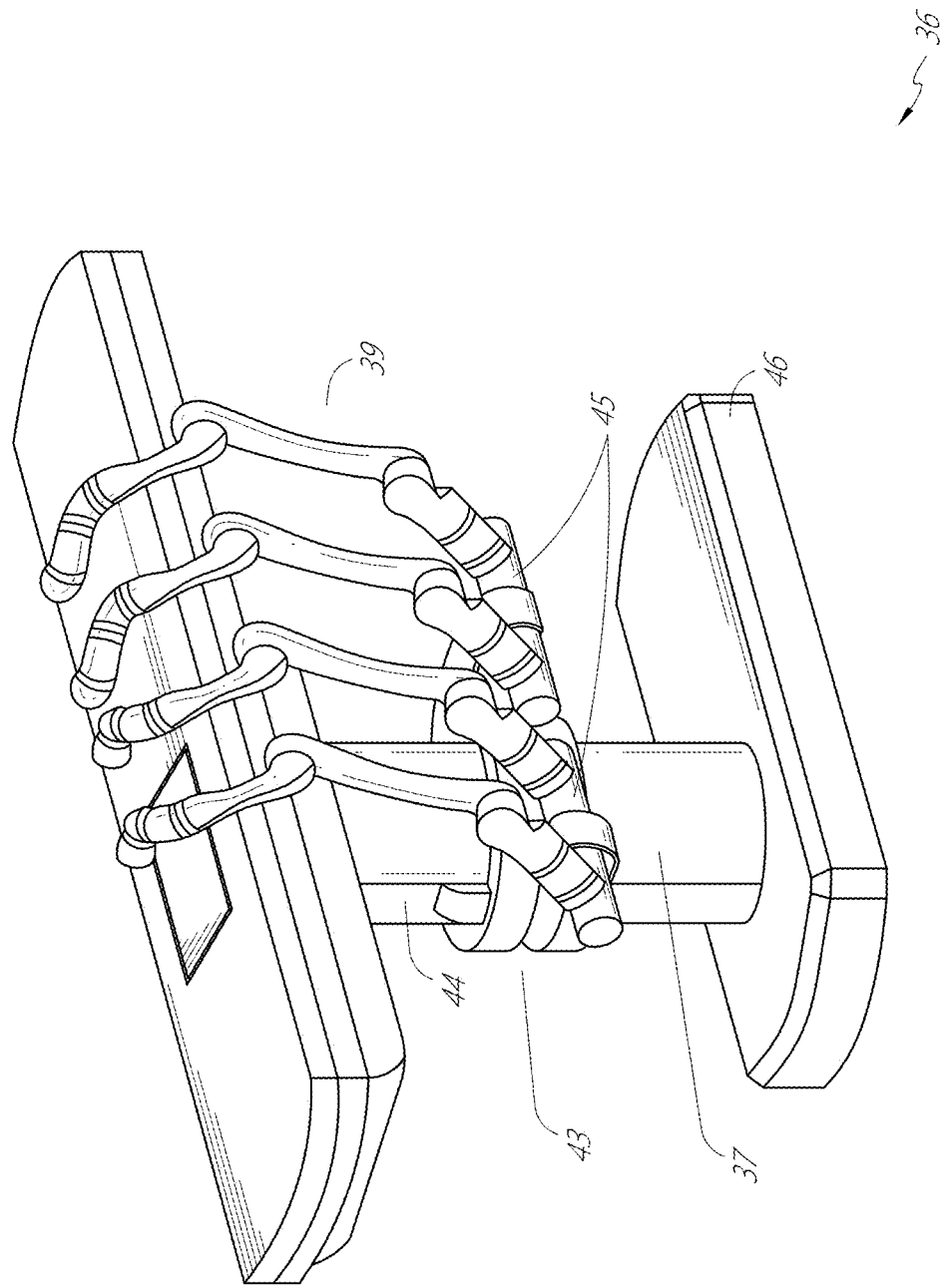
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
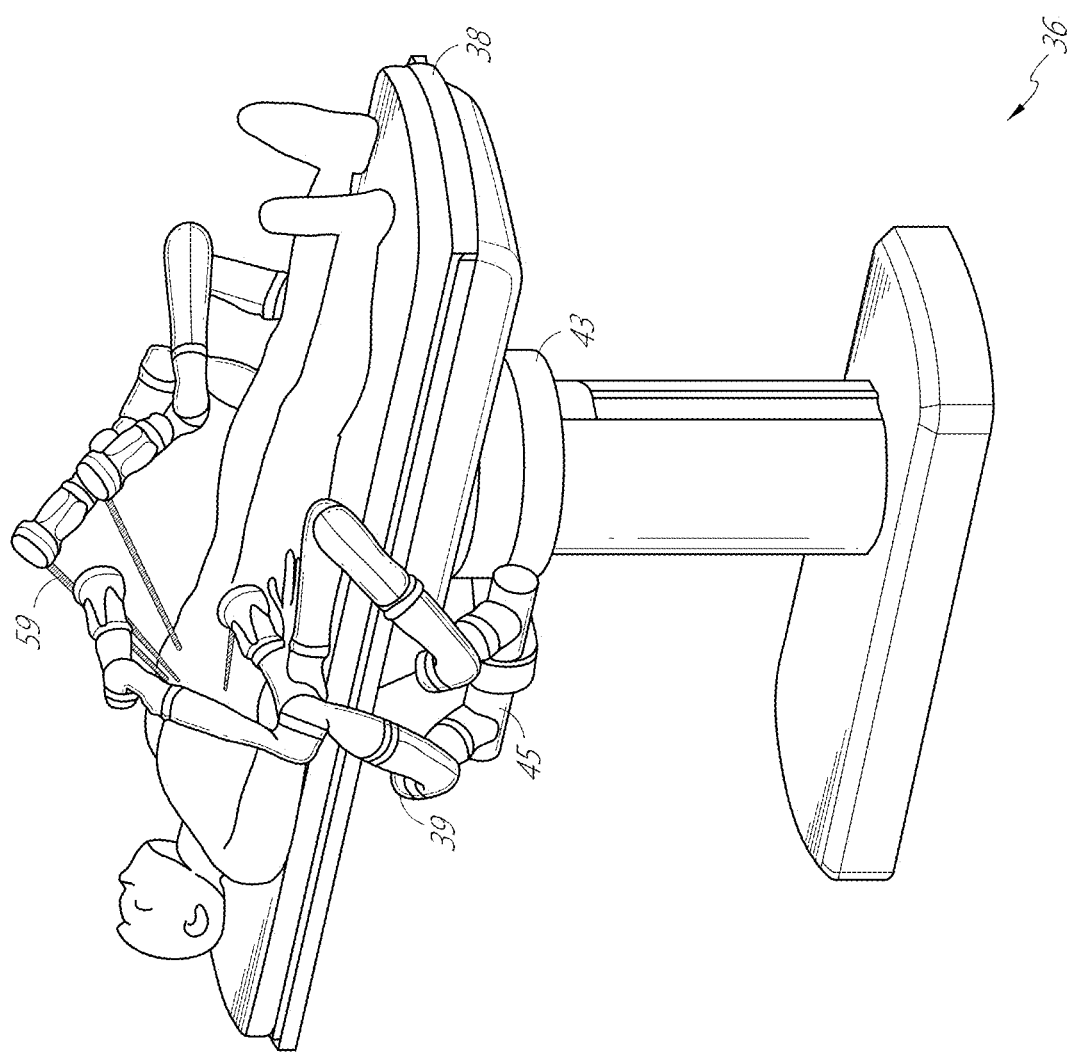
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
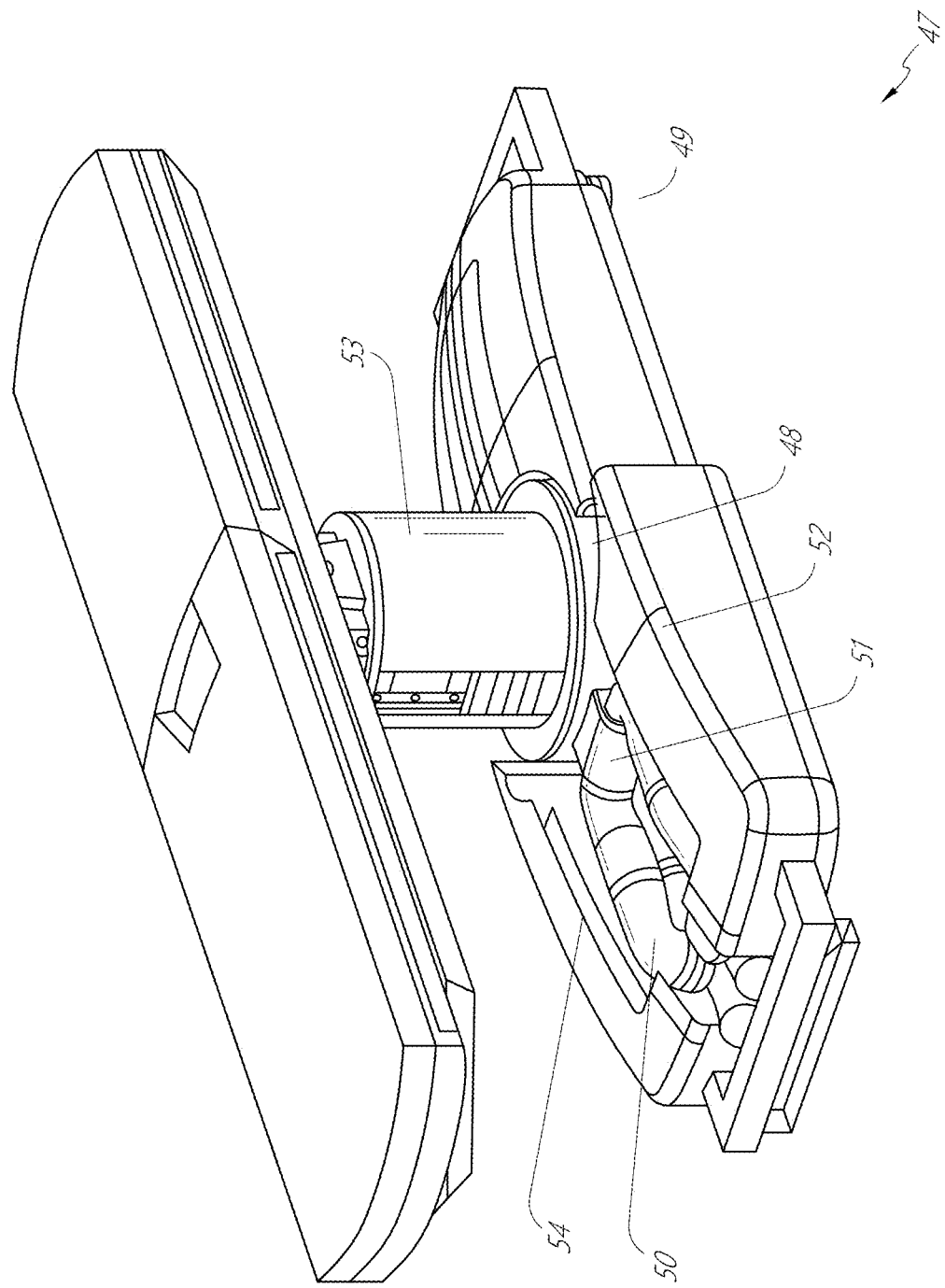
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
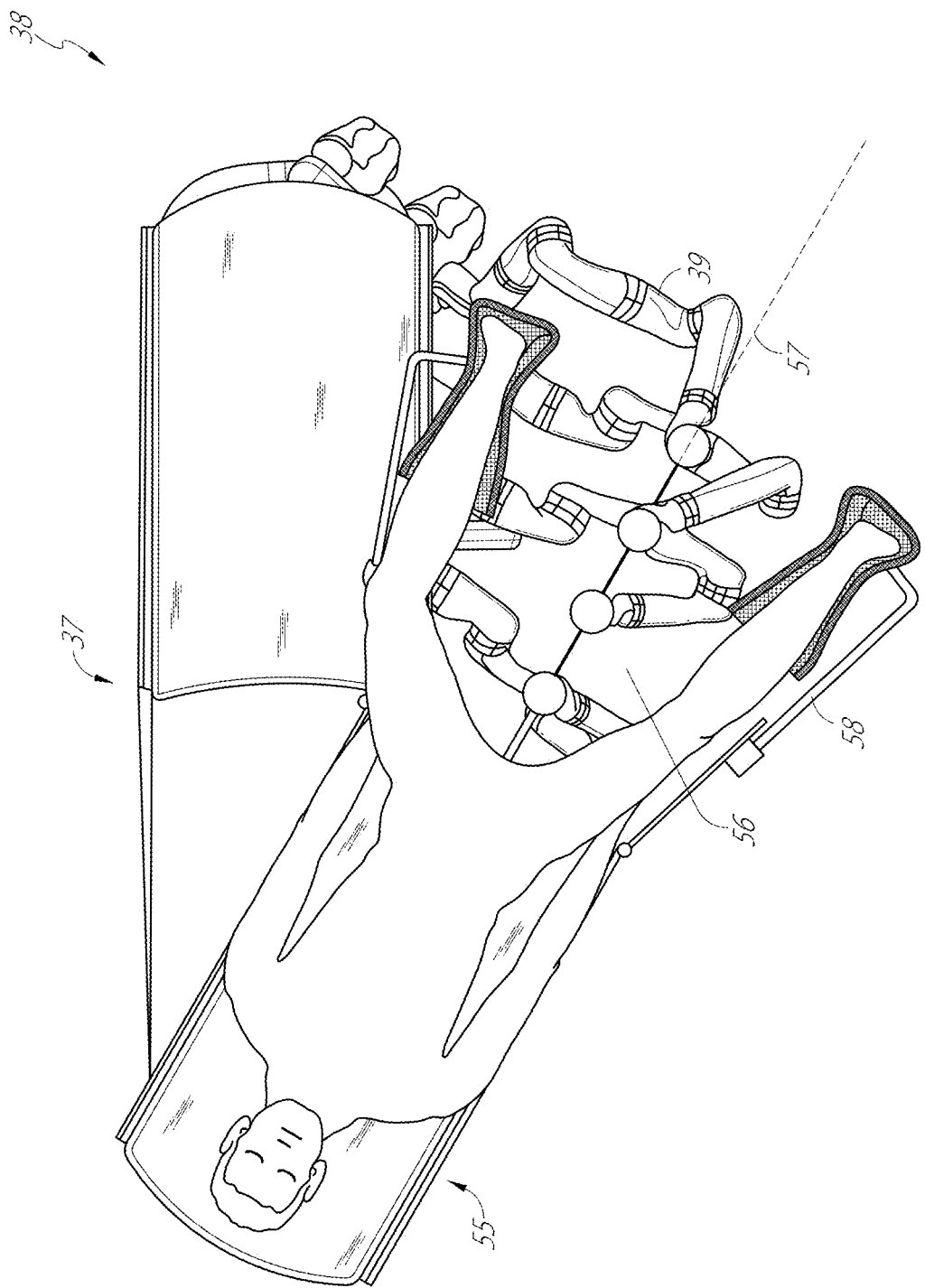
FIG. 8 illustrates an embodiment of a table-based robotic system configured for a ureteroscopic procedure.

FIG. 8 illustrates an embodiment of a robotically enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
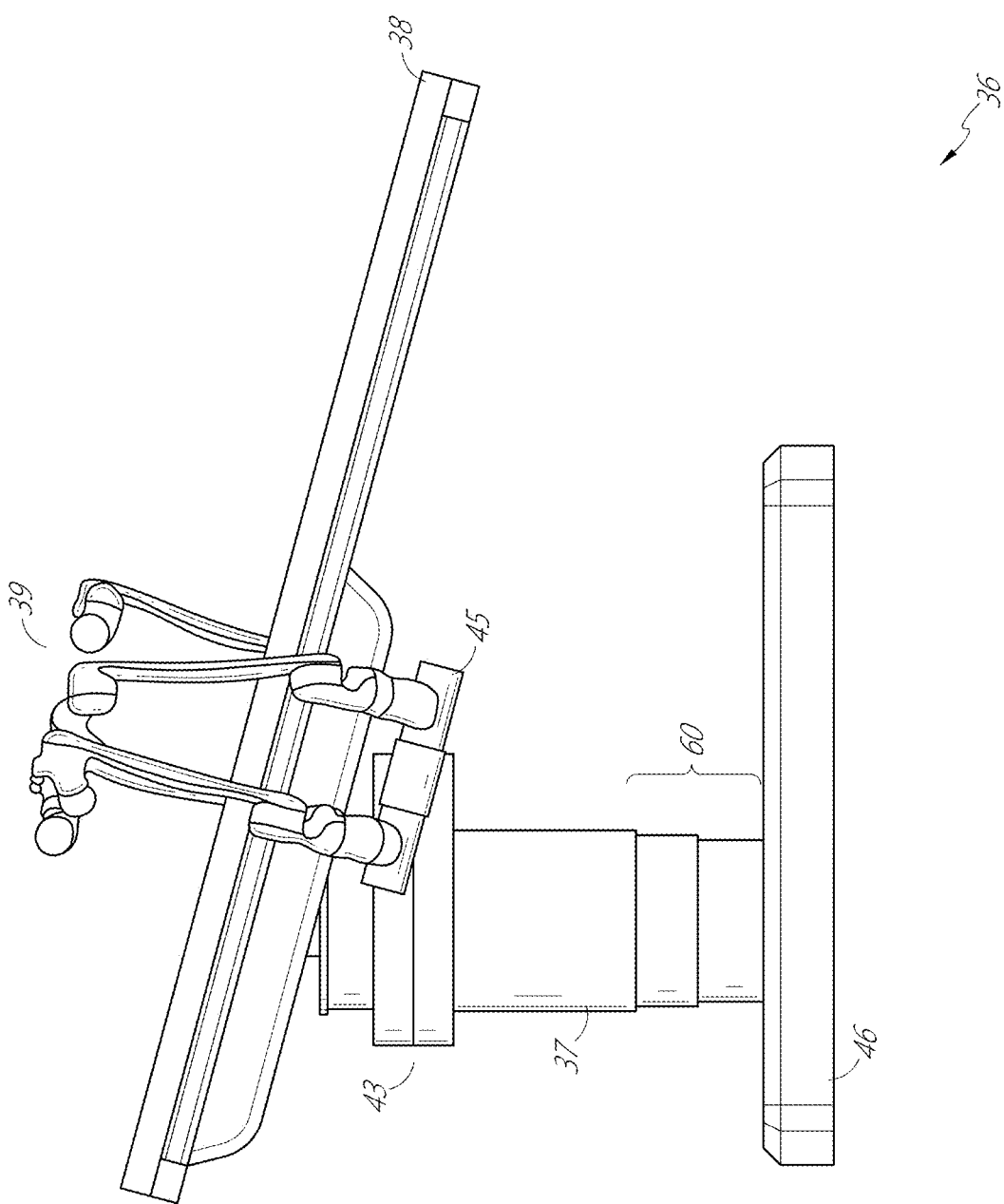
FIG. 10 illustrates an embodiment of the table-based robotic system of FIGS. 5-9 with pitch or tilt adjustment.

To accommodate laparoscopic procedures, the robotically enabled table system may also tilt the platform to a desired angle. FIG. 10 illustrates an embodiment of the robotically enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
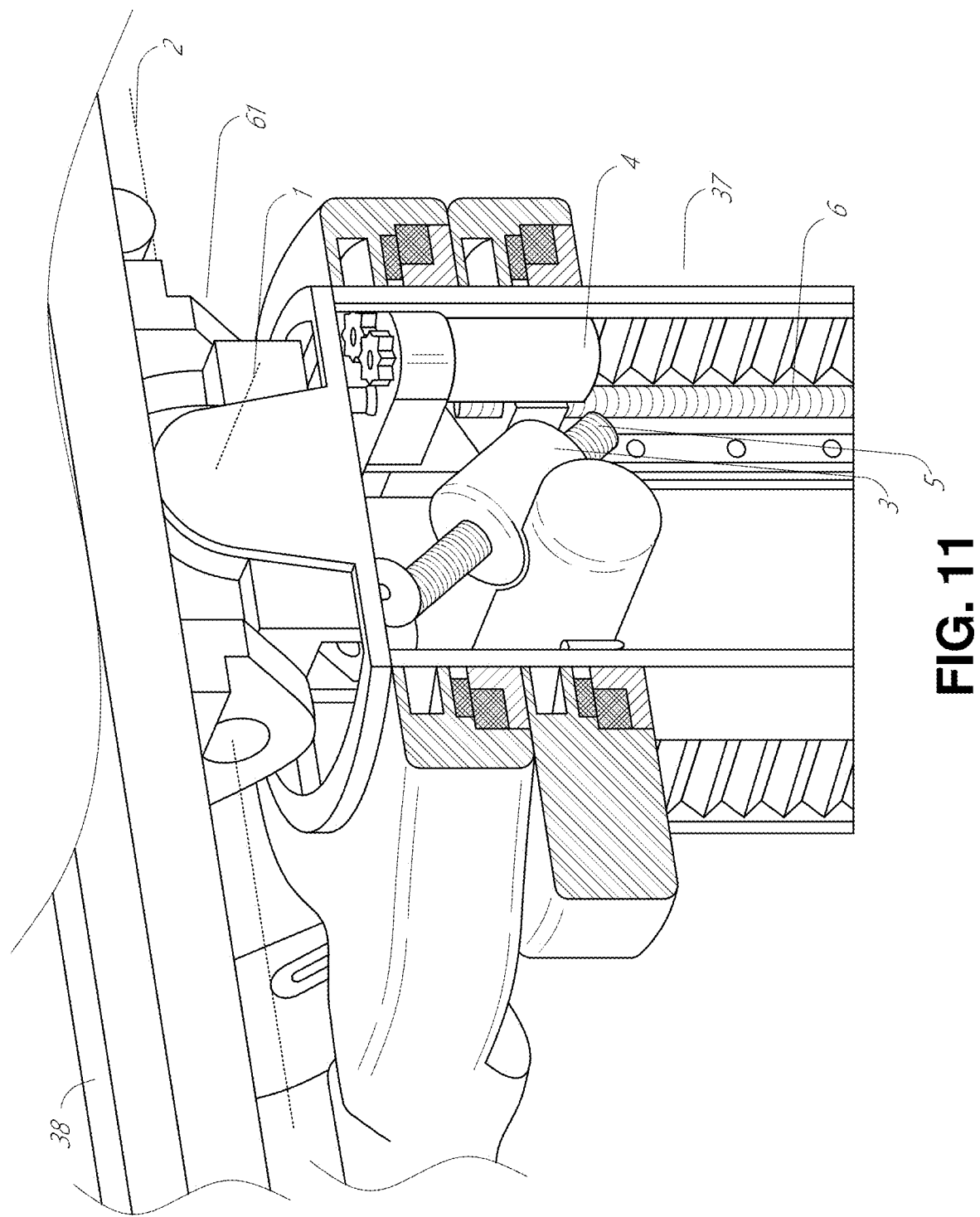
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
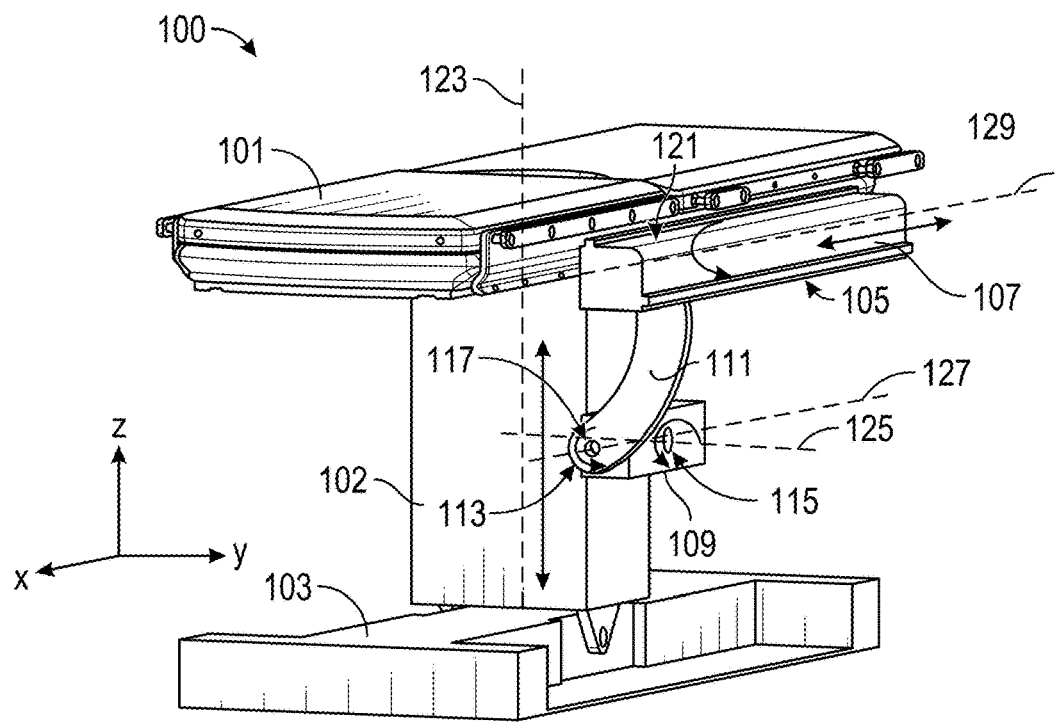
FIG. 12 illustrates an alternative embodiment of a table-based robotic system.
Figure 13:
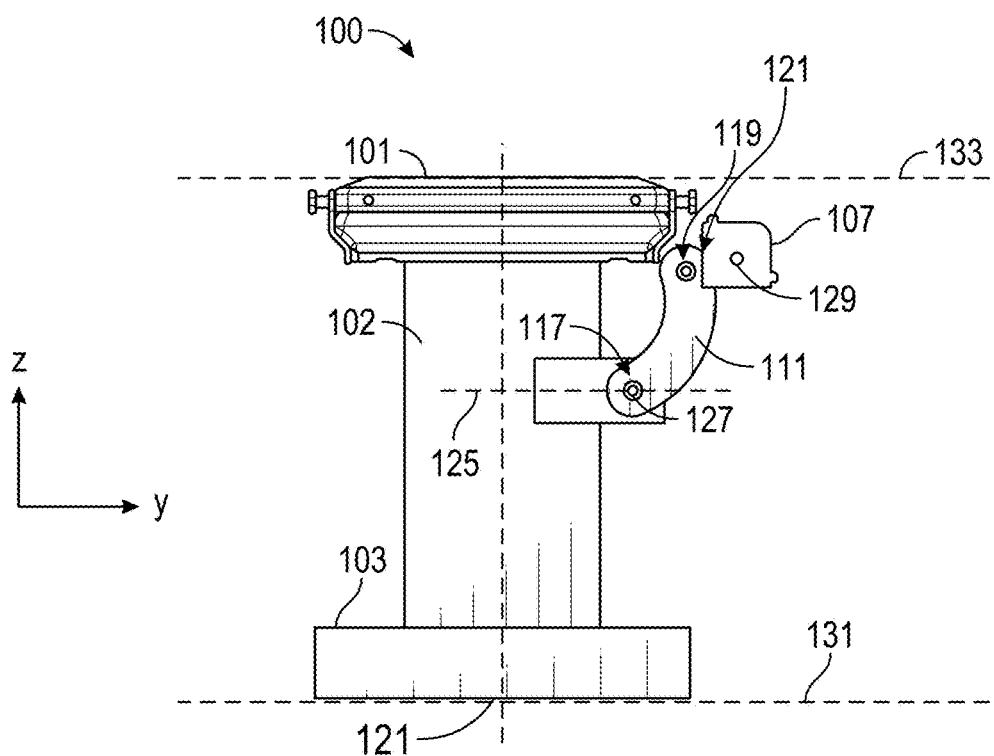
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
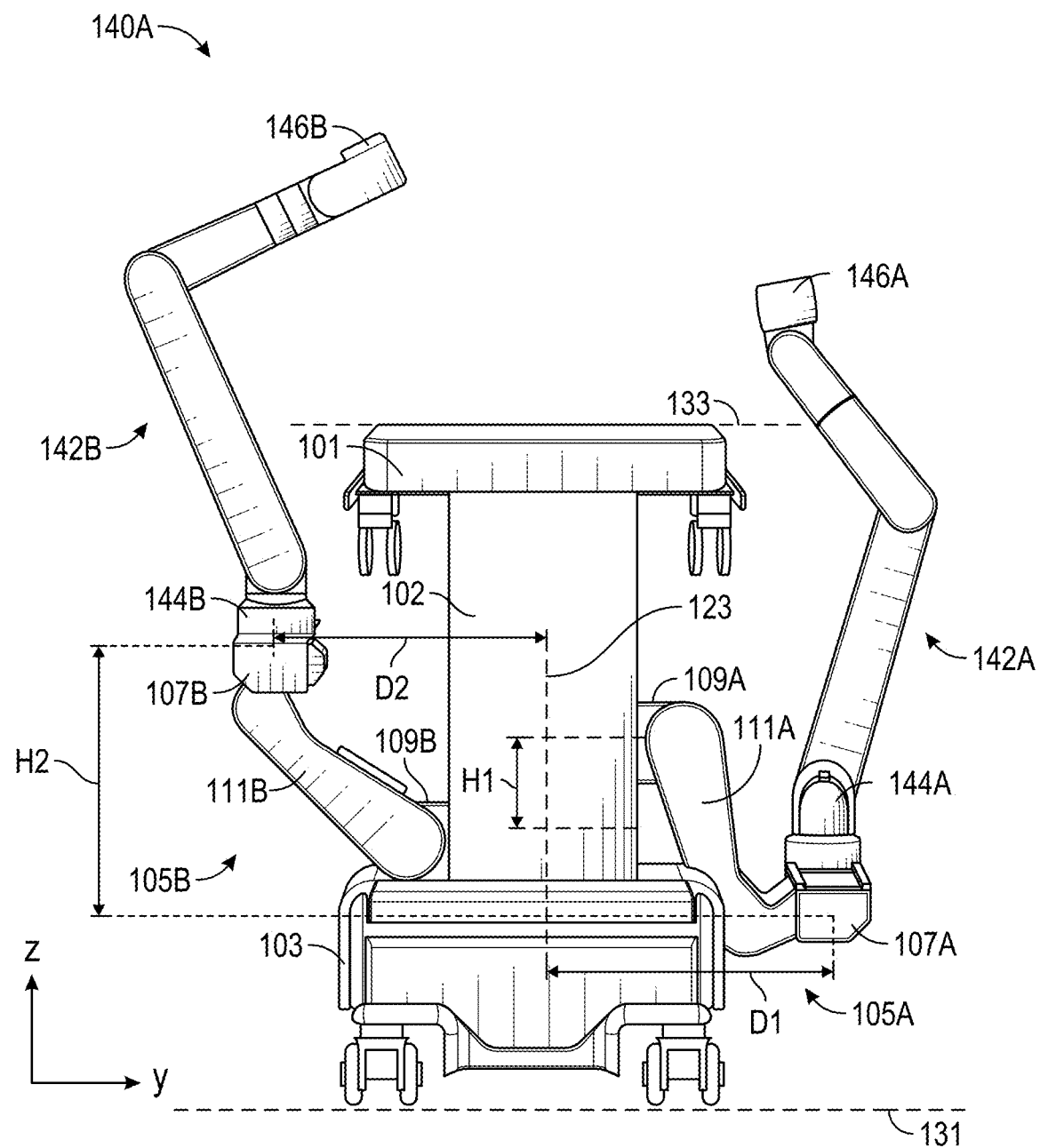
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface

The end effectors of the system's robotic arms may comprise (i) an instrument driver (alternatively referred to as "instrument drive mechanism," "instrument device manipulator," or "advanced device manipulator (ADM)") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
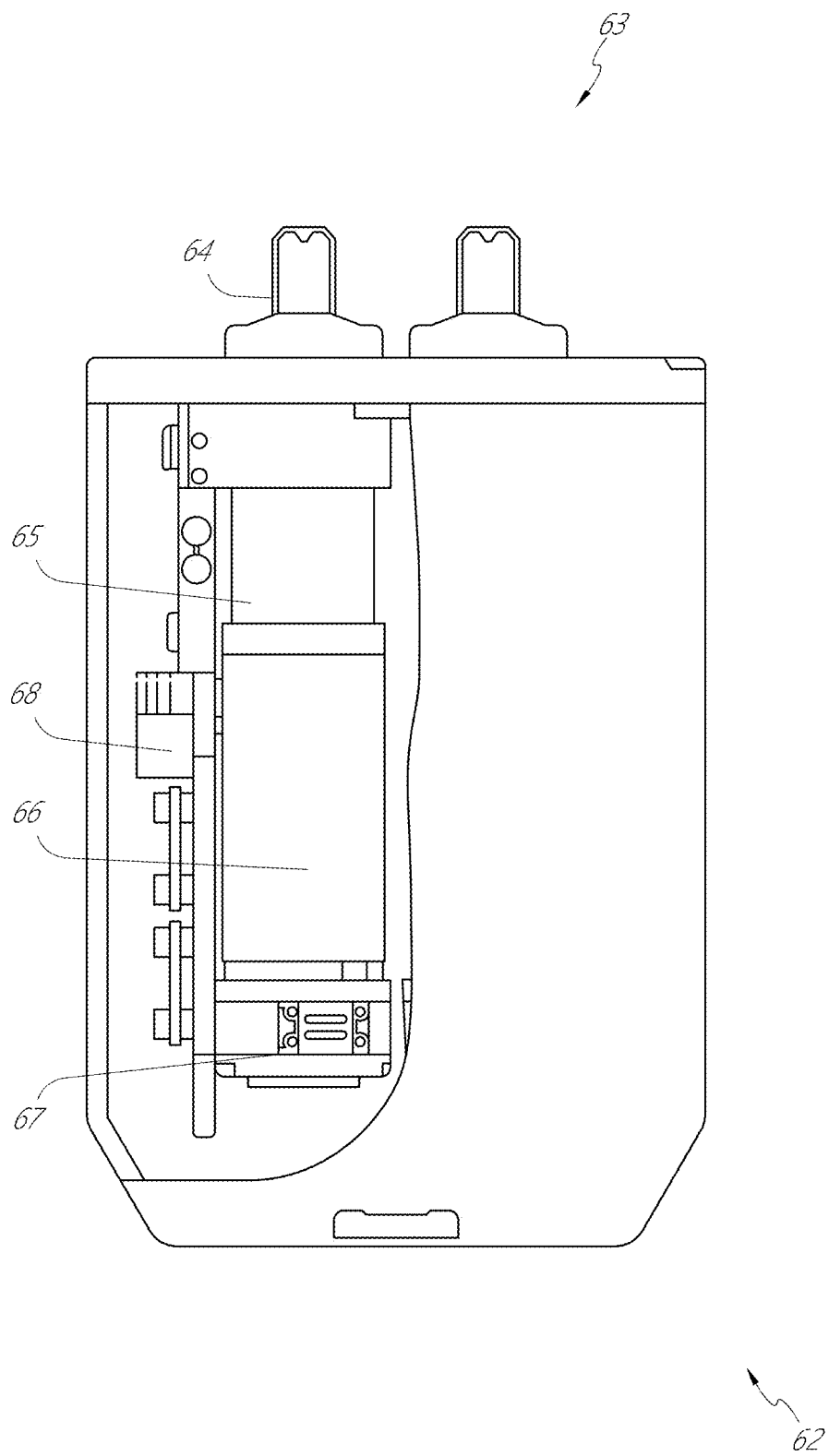
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument

Figure 16:
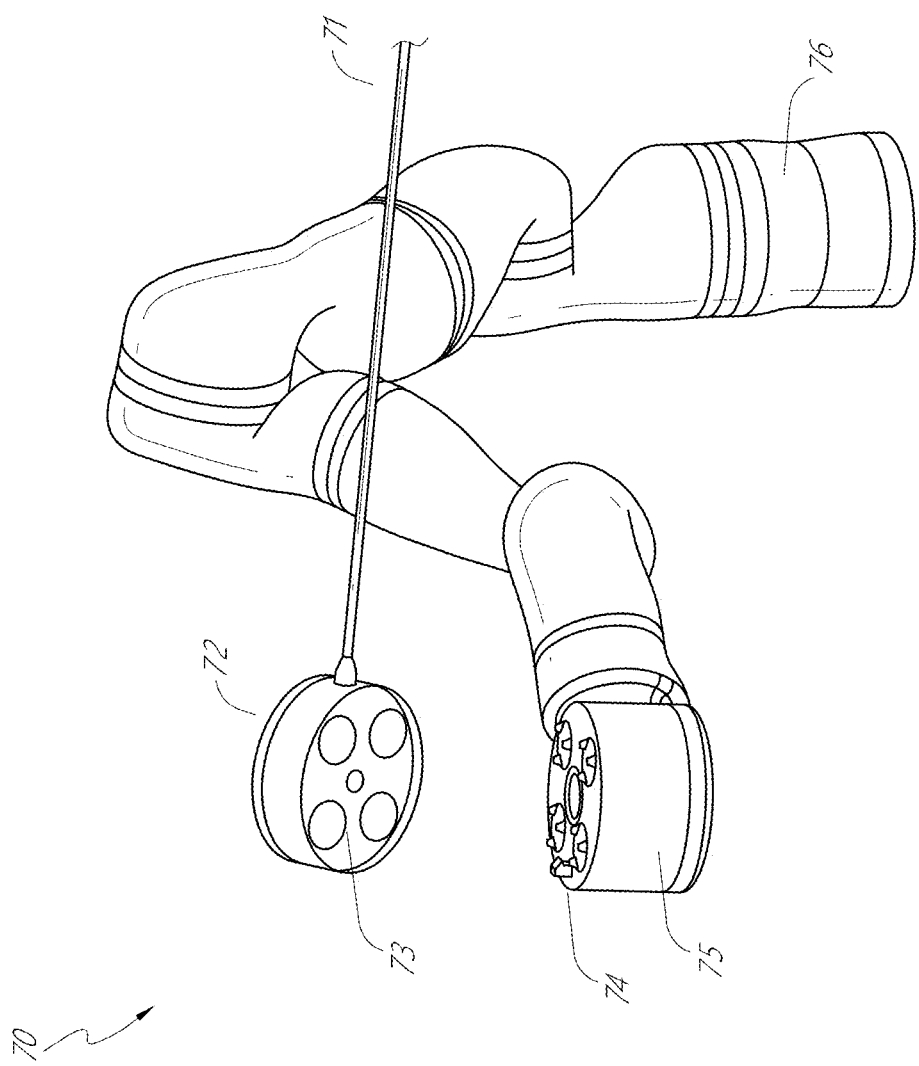
FIG. 16 illustrates an exemplary medical instrument with a paired instrument driver.

FIG. 16 illustrates an example medical instrument with a paired instrument driver Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
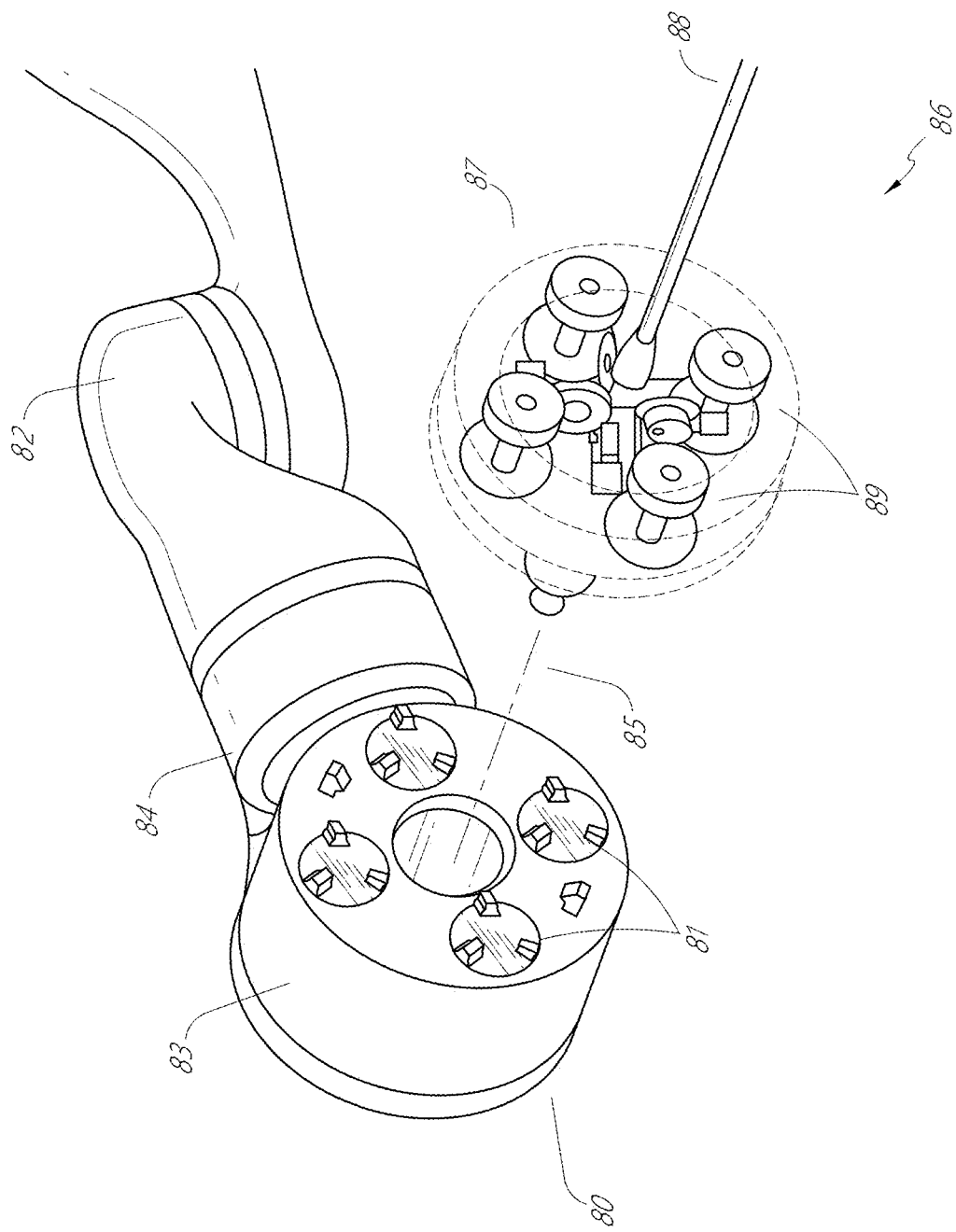
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
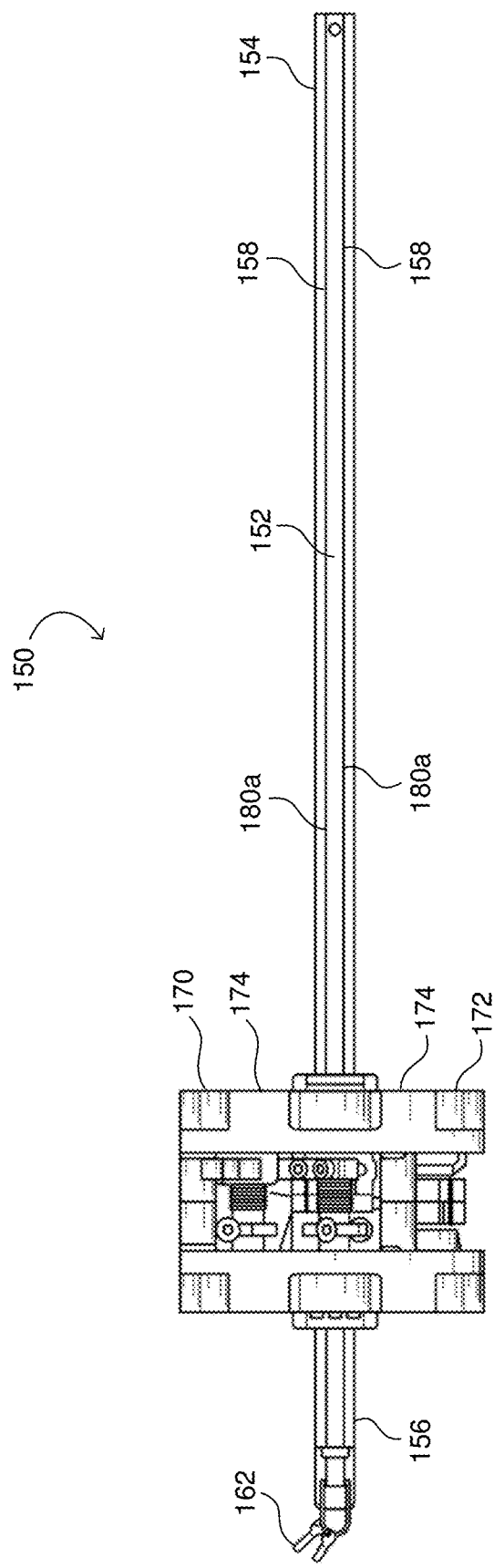
FIG. 18 illustrates an instrument having an instrument-based insertion architecture.

FIG. 18 illustrates an instrument having an instrument-based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
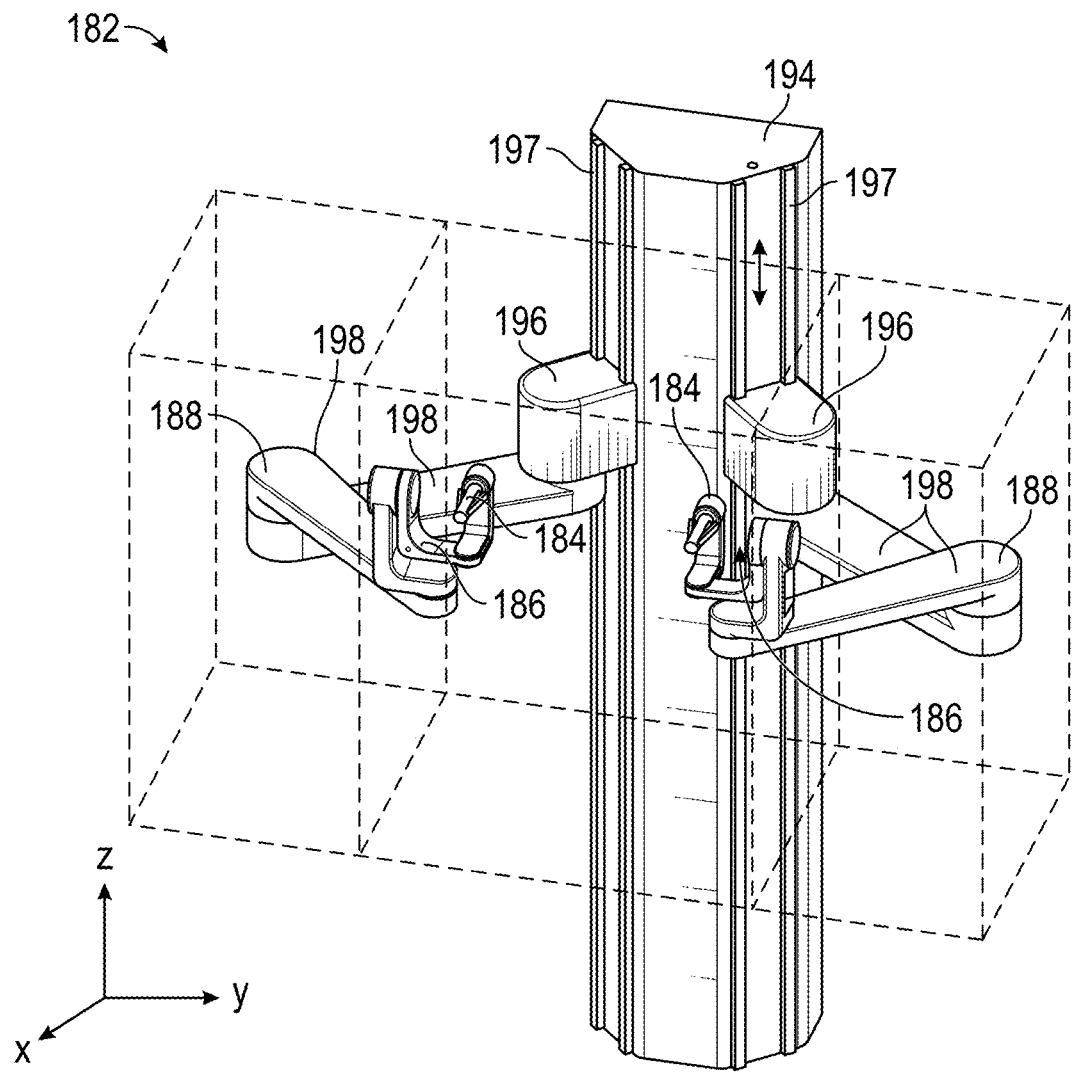
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
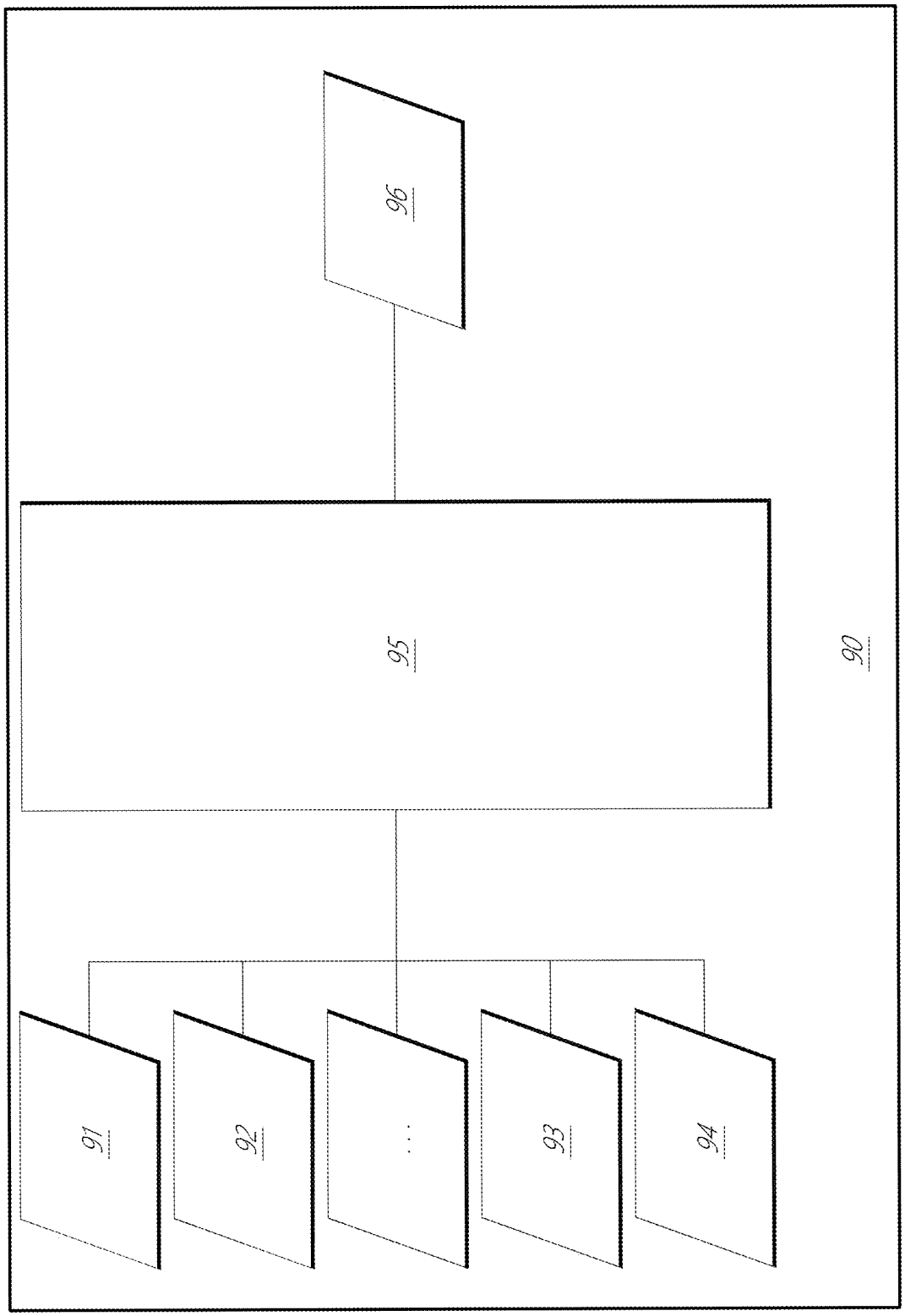
FIG. 20 depicts a block diagram illustrating a localization system that estimates a location of one or more elements of the robotic systems of FIGS. 1-10, such as the location of the instrument of FIGS. 16-18, in accordance with an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images and are particularly appropriate for bronchoscopy.

In some embodiments, the instrument may be equipped with a camera to provide vision data (or image data) 92. The localization module 95 may process the vision data to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter) may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Robotic Arm Alignment and Docking

Embodiments of the disclosure relate to systems and techniques for computer assisted alignment and/or docking of robotic arm(s) to a target of a patient. As previously discussed, prior to introducing a surgical instrument into a patient, a robotic arm may be aligned and/or docked with a target (e.g., a port which is installed or otherwise placed in the patient). After docking, the robotic arm and/or system may be configured to control the movement of a distal end of an instrument while maintaining a remote center of motion.

Figure 21:
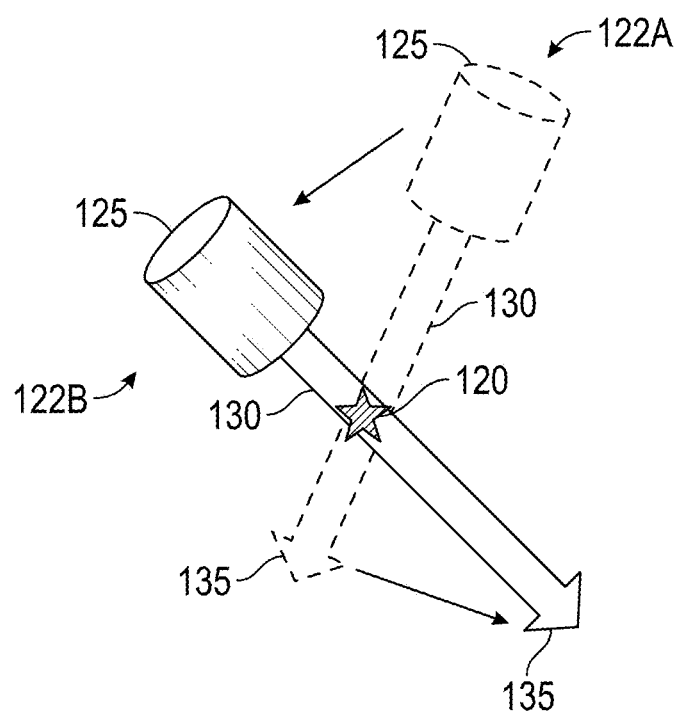
FIG. 21 illustrates exemplary movement of an ADM 105 while maintaining a remote center of motion in accordance with aspects of this disclosure.

FIG. 21 illustrates exemplary movement of an ADM 125 while maintaining a remote center of motion in accordance with aspects of this disclosure. FIG. 21 illustrates the ADM 125, an instrument 130, and a distal end 135 of the instrument 130. In particular, FIG. 21 illustrates the movement of the ADM 125 from a first position 122A to a second position 122B while maintaining a remote center of motion 120. The ADM 125 can be coupled to a distal end of a robotic arm (such as those shown in FIG. 14) configured to control movement of the ADM 125 and the distal end 135 of the instrument 130.

The robotic arm and/or surgical system can establish and maintain the position of the remote center of motion 120 for the instrument 130. Depending on the embodiment, the remote center of motion 120 can be maintained either mechanically or by software execute on one or more processors of the system. During a surgical procedure, the instrument 130 may be inserted through the patient's body wall to gain access to an internal region of the patient. The remote center of motion 120 may be defined at the intersection between the body wall and the instrument in order to prevent and/or reduce movement of the body wall during the procedure, thereby enabling the surgical procedure to safely take place. For example, if the location of the intersection between the instrument is not held substantially stationary during the procedure, the instrument may apply unnecessary force to the body wall, potentially tearing the body wall. Thus, it is desirable to maintain the remote center of motion 120 to prevent unnecessary forces from being applied to the body wall.

There may be a number of challenges associated with docking an ADM to a port installed or placed in the patient. For example, the surgical environment may include a plurality of other robotic arms, sterile drapes, and other surgical equipment, which may obscure the view of the robotic arm and/or port and limit the range of motion available for the docking procedure. Thus, manual docking of the robotic arm and/or ADM to or with the port may be a time-consuming and difficult procedure. The docking procedure can therefore be time-consuming and can require numerous adjustments and interaction with the robotic arm in a confined space. Due to the time-consuming nature of the docking procedure, surgeons may choose sub-optimal port locations that will accommodate larger workspaces to reduce the chance that a port location will need to be moved during the surgical procedure and require undocking and re-docking of the robotic arm.

Aspects of this disclosure relate to methods and systems that may automate at least a portion of the docking process. Certain aspects may provide advantages including automating at least a portion of the docking process and reducing the reliance on health care providers to manually dock robotic arms to ports.

A. Alignment and Docking Techniques

Figure 22:
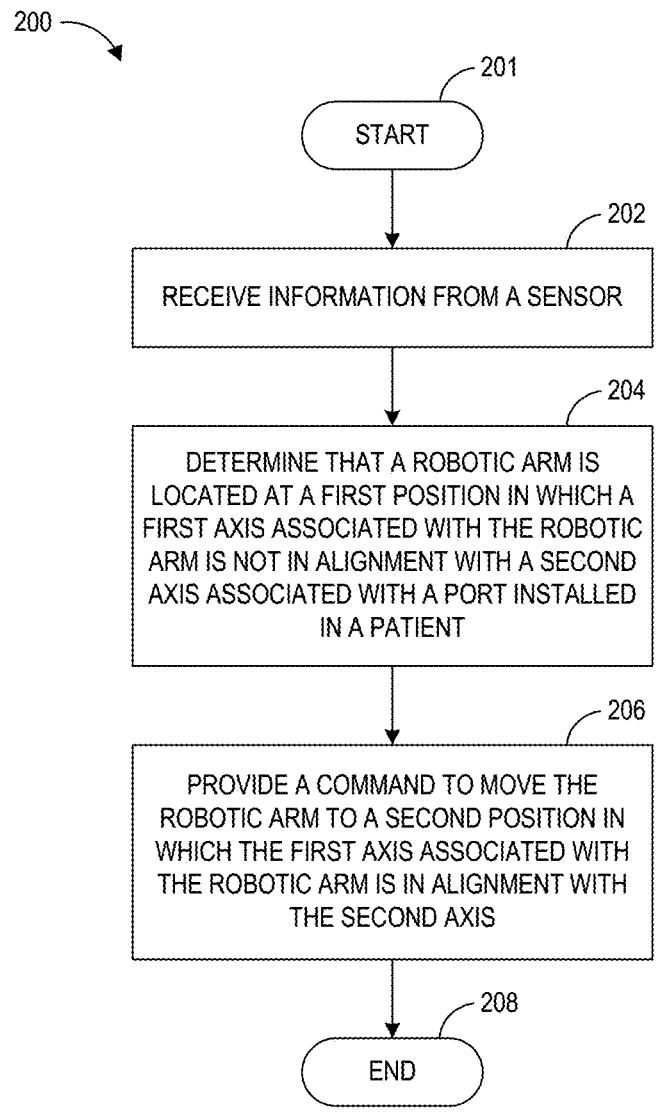
FIG. 22 is a flowchart illustrating an example technique for aligning a robotic arm with a port in accordance with aspects of this disclosure.

Aspects of this disclosure involve the use of one or more sensors to assist in alignment and docking of a robotic arm with a target of a patient. The docking procedure may involve moving the robotic arm to align a first axis associated with the robotic arm into alignment with a second axis associated with the target. FIG. 22 is a flowchart illustrating an example method operable by a surgical robotic system, or component(s) thereof, for aligning a robotic arm with a port in accordance with aspects of this disclosure. Although the procedure described in connection with FIG. 22 may involve the docking of the robotic arm with a port, in other embodiments, the robotic arm may instead be aligned with an access point of the patient, where the access point does not include a port placed or installed in the patient (e.g., a natural orifice such as the patient's sinus).

The steps of method 200 illustrated in FIG. 22 may be performed by a processor of a surgical robotic system. For convenience, the method 200 is described as performed by the processor of the system. The processor may be included as a part of a system, including a robotic arm (e.g., the robotic arm(s) 12 of FIGS. 1-4) and one or more sensors configured to generate information indicative of a location and/or pose of the robotic arm. In some embodiments, the sensor can be an image sensor (e.g., a camera) that can be attached to the robotic arm (e.g., attached to an ADM located at a distal end of the robotic arm). However, in other embodiments, any other type of sensor (e.g., an EM sensor, an infrared (IR) sensor, a Light Detection and Ranging (LIDAR) sensor, and/or a radio frequency (RF) sensor) can be used. In alternative embodiments, the sensor can be positioned in other locations within the operating environment other than at the ADM. For example, the sensor may be mounted to a bed or cart or may be mounted to another robotic arm other than the robotic arm currently being docked.

As is described in detail below, the sensor can be used to detect and identify a fiducial that is associated with the port or access point. As used herein, a fiducial may refer to a marking or object that can be detected by the sensor and used by the system to determine the relative spatial position between the fiducial and the sensor. For example, when the sensor is embodied as an image sensor, the fiducial may include a marking or other visual pattern detectable by the image sensor. In the EM sensor embodiments, the fiducial may include an EM emitter and/or reflector that radiates an EM signal detectable by the EM sensor. The processor may be configured to determine the orientation and position of the fiducial relative to the sensor based on a signal produced by the sensor. In certain embodiments, the fiducial can be positioned on the patient in a defined relative position with an access point in which the port is located.

Referring back to FIG. 22, the method 200 begins at block 201. At block 202, the processor receives information indicative of a location of the robotic arm from the sensor. The information may define the relative spatial position of the robotic arm with respect to the fiducial. Since the fiducial may be located at a predetermined relative position with respect to the port, the processor may be able to determine the relative positions of the robotic arm and the port.

At block 204, the processor determines that the robotic arm is located at a first position in which a first axis associated with the robotic arm is not in alignment with a second axis associated with a port installed in a patient. Here, the first axis may comprise a tool path axis along which a tool is configured to be inserted/retracted by the robotic arm, and the second axis may comprise an insertion axis of the port through which the tool can be inserted. At block 206, the processor provides a command to move the robotic arm to a second position in which the tool path axis associated with the robotic arm is in alignment with the insertion axis. Accordingly, the processor may be able to determine the motion of the robotic arm which will bring the robotic arm into alignment with the port. In certain embodiments, the system may include a user input (e.g., a button or switch) configured to control the alignment/docking process. For example, the system may receive a command from the user to automatically align and/or dock the robotic arm to the port by moving the robotic arm from the first position in which the tool path axis of the robotic arm is not in alignment with the insertion axis of the port to the second position in which the tool path axis is aligned with the insertion axis.

With the tool path axis aligned with the insertion axis, the processor may move the robotic arm towards the port along the insertion axis. The processor may bring a portion of the robotic arm (e.g., an ADM formed at the distal end of the robotic arm) within a threshold distance of the port to allow the ADM to be docked to the port. In certain embodiments, the final docking (e.g., coupling or latching) of the ADM to the port may be performed manually. In other embodiments, docking may be performed automatically under control of the processor and/or may involve automatically placing the ADM in close spatial proximity to the port without physically coupling the ADM to the port. The method ends at block 208.

Figure 23:
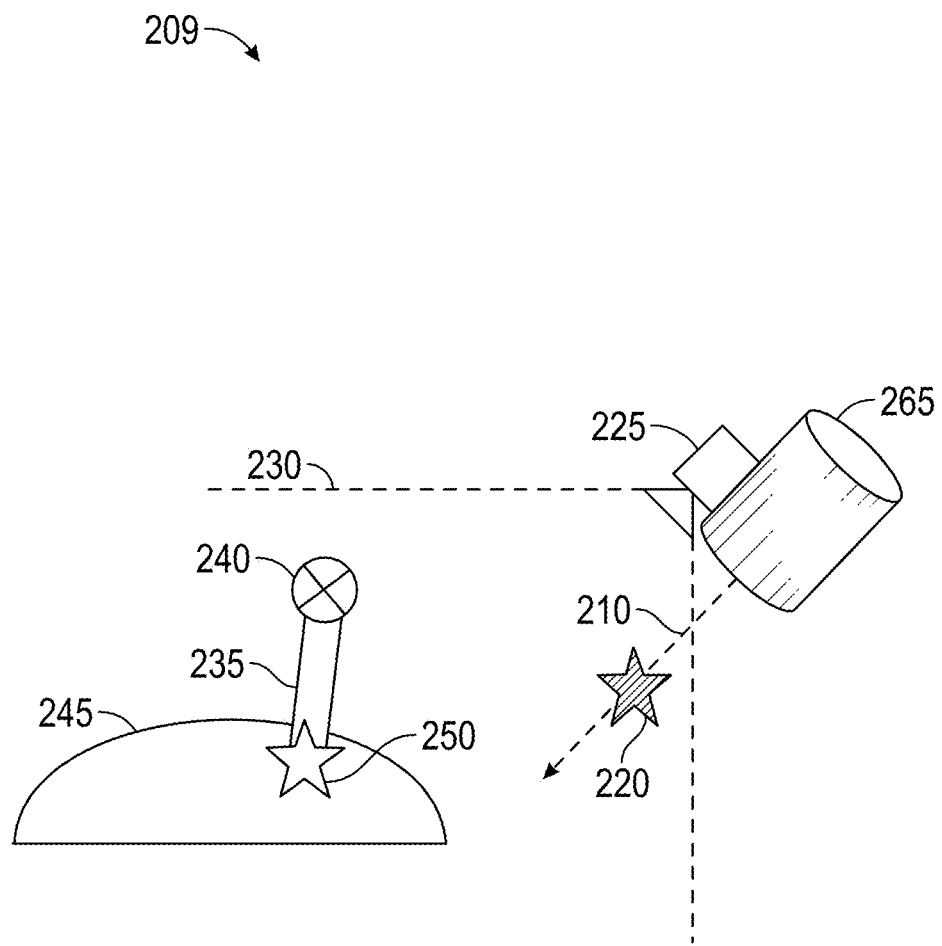
FIG. 23 illustrates a robotic arm and a port at a first position in an exemplary docking method in accordance with aspects of this disclosure.
Figure 24:
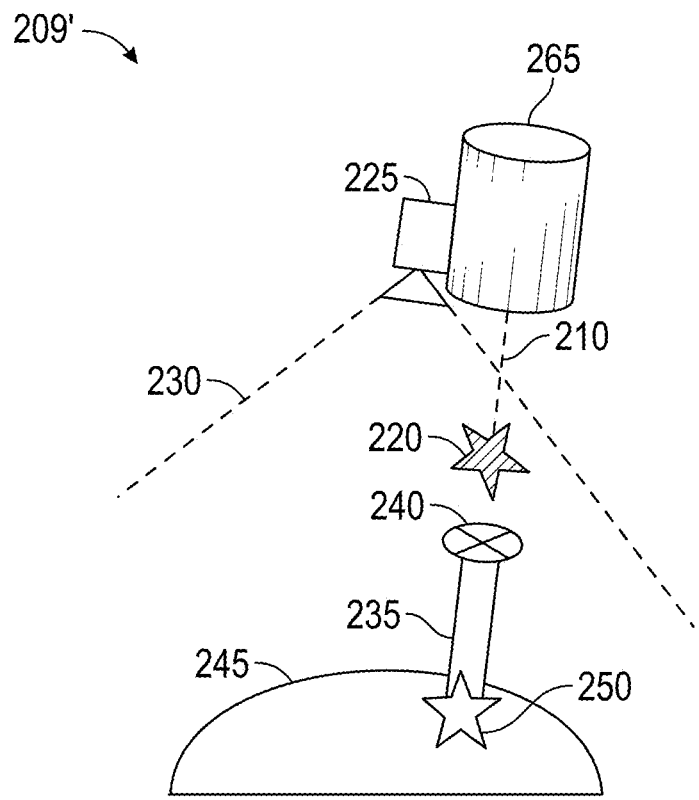
FIG. 24 illustrates the robotic arm and the port at a second position in the exemplary docking method in accordance with aspects of this disclosure.
Figure 25:
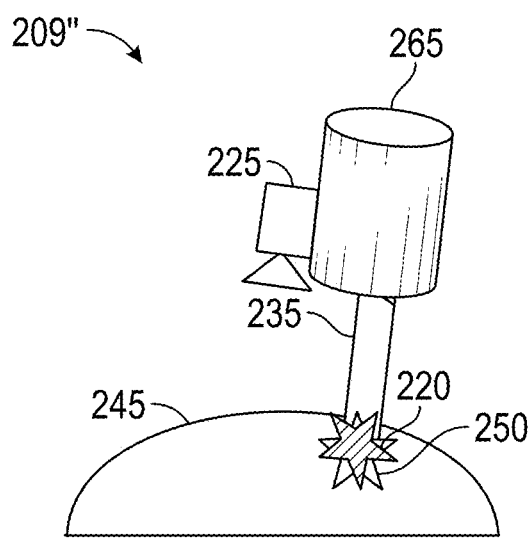
FIG. 25 illustrates the robotic arm and the port at a third position in the exemplary docking method in accordance with aspects of this disclosure.

FIGS. 23-25 illustrate various stages of an exemplary docking method or technique in accordance with aspects of this disclosure. In general, FIG. 23 illustrates a portion of a robotic system 209 which includes an ADM 265 of a robotic arm (not illustrated) in a first position with respect to a port 235, whereas FIG. 24 illustrates the system 209' with the ADM 265 at a second position with respect to the port 235, and whereas FIG. 25 illustrates the system 209" with the ADM 265 in a third position with respect to the port 235. The exemplary method illustrated in FIGS. 23-25 may involve the use of an image sensor 225 (e.g., a camera) attached to an ADM 265. However, in other embodiments, another type of sensor may be used (e.g., an EM sensor, an IR sensor, a LIDAR sensor, and/or an RF sensor) and the sensor may be located in a location other than on the ADM (e.g., attached or mounted to the robotic arm, the bed, a cart, etc.).

With reference to FIG. 23, the system 209 according to one embodiment includes the ADM 265, a tool path 210 associated with the ADM 265, a remote center of motion 220 (represented with a star symbol for illustrative purposes), and the image sensor 225 having an associated field of view 230. The system 209 may further include a port 235, a fiducial 240 on the port 235, a body wall 245 of a patient, and a point of intersection 250 between the port 235 and the body wall 245. The ADM 265 is attached to the distal end of a robotic arm (not illustrated) configured to control movement of the ADM 265 and an instrument (not illustrated) which can be inserted and retracted along the tool path 210. As shown in FIG. 23, at the first position, the tool path axis 210 is in alignment with an insertion axis of the port 235 (e.g., a longitudinal axis of the port 235). In the present embodiment, the image sensor 225 is shown coupled to an outer side wall of the ADM 265, while in other embodiments, the image sensor 225 can be found in other locations, e.g., within the body of the ADM 265 itself. In some embodiments, the image sensor 225 can be detachably coupled with the ADM 265, while in other embodiments, the image sensor 225 can be integrated with the ADM 265.

During set-up of the surgical environment, the robotic arm and the ADM 265 may be located at a defined distance from the port 235, and the ADM 265 may not be in alignment with the port 235. As an initial step of the alignment method, the user may manually position the ADM 265 into the first position such that the fiducial 240 is within the field of view 230 of the image sensor 225. In another embodiment, the movement of the ADM 265 into the first position may be performed automatically by the robotic system 209. Once the fiducial 240 is within the field of view 230 of the image sensor 225, the system 209 may be able to use the images received from the image sensor 225 to determine the relative position between the ADM 265 and the port 235.

Using the images received from the image sensor 225 as an input, a processor and/or controller of the robotic system 209' may provide instructions to the robotic arm to move the ADM 265 from the first position to the second position illustrated in FIG. 24. In the second position, the tool path axis 220 is substantially aligned with the insertion axis of the port 235. For example, the degree of alignment between the tool path axis 220 and the insertion axis of the port 235 (or acceptable level of alignment) may be selected, e.g., by a user of the robotic system. The processor may be able to determine both the relative location and orientation of the fiducial 240 relative to the image sensor 225 (and/or another part of the ADM 265) based on the images received from the image sensor 225. The processor may also use data indicative of the relative location of the fiducial 240 with respect to the port 235 and the relative location of the image sensor 225 with respect to the ADM 265 to determine the relative location of the fiducial 240 with respect to the ADM 265. For example, techniques for determining the relative location of a fiducial 240 with respect to a camera/ADM 265 is discussed below in connection with FIGS. 32A and 32B.

After the tool path axis 220 is aligned with the insertion axis at the second position of FIG. 24, the system 209" may provide instructions to the robotic arm to move the ADM 265 towards the port 235 along the insertion axis as illustrated in FIG. 25. FIG. 25 illustrates the position of the ADM 265 with respect to the port 235 after alignment and docking is completed. For example, the remote center of motion 220 may be substantially aligned or overlap with the intersection point 250. For example, the degree of alignment between the remote center of motion 220 and the insertion point 250 (or acceptable level of alignment) may be selected, e.g., by a user of the robotic system.

In certain embodiments, the processor may command the robotic arm to bring the ADM 265 within a threshold distance of the port 235 to allow the ADM 265 to be docked to the port 235. Once the ADM 265 is within a threshold distance of the port 235, the ADM 265 may be secured to the port 235 in an automated mode by the robotic system and/or manually by the user (or another person helping the user). In some embodiments, the distance between the ADM 265 and the port 235 may be determined based on the distance between the remote center of motion 220 and the intersection point 250. In related aspects, docking (e.g., coupling or latching) of the ADM 265 to the port 235 may, e.g., be performed manually. In addition, or in the alternative, the docking may be performed automatically under control of the processor and/or may involve placing the ADM 265 in close spatial proximity to (i.e., within a defined distance or area of) the port 235 without physically coupling the ADM 265 to the port 235. Once the ADM 265 is docked to the port 235, an instrument can inserted through the ADM 265 and the port 235 to gain access to an internal region of the patient.

In certain implementations, the ADM 265 may be part of an instrument-based insertion architecture, and may be connected to an instrument, such as, e.g., the instrument 150 illustrated in FIG. 18. Accordingly, a handle (e.g., the handle 170) of the instrument can be coupled to the ADM 265, allowing the instrument to be inserted into the patient via the port 235 while the ADM 265 and handle remain in place. In other words, the instrument can be configured to translate with respect to the ADM 265 and handle. The ADM 265 may include mechanical outputs that are configured to be coupled to mechanical inputs on the handle, at least some of which can control the insertion of the instrument with respect to the handle. In other implementations, the ADM 265 may comprise the instrument driver 75 to which an instrument base or handle 72 may be attached, as illustrated in FIG. 16.

The method described above in connection with FIGS. 23-25 is different from entirely manual docking techniques. For example, a manual docking procedure may be difficult for a user to perform due to other objects in the operating environment which may limit the range of movement of the robotic arm and/or limit the user's field of view. For example, other robotic arms, sterile drapes coupled to the robotic arms, etc. may interfere with the user's ability to manually dock an ADM 265 to a port 235. In some embodiments, when the tool path axis 210 is brought into alignment with the insertion axis of the port 235, the processor may actuate an indicator (e.g., a light or haptic feedback on a master controller, e.g., the controller 182 of FIG. 19) to provide feedback to a user regarding the alignment, in order to facilitate manual alignment performed by the user.

The method described in connection with FIGS. 23-25 is one example of using one type of sensor (e.g., an image sensor 225) to detect the relative spatial position of a port 235 during the alignment/docking of the robotic arm and ADM 265. However, aspects of this disclosure also relate to the user of other sensor types, which may involve the use of different fiducials. Similarly, other modes of user control including differing levels of automation may also be employed. Example sensors which can be used to determine the relative position of the ADM and the port include an EM sensor, an IR sensor, a LIDAR sensor, and/or an RF sensor. One or more of the sensors can be mounted on the robot arm (e.g., on the ADM), on instruments, and/or at other locations within the operating room. Likewise, fiducials need not be placed on the port itself. For example, fiducials can be placed on the patient and/or on a draping in a known relative spatial position and orientation with respect relation to the port. In some embodiments, the alignment and docking process can be fully automated. In some embodiments, the alignment and docking process can be performed while a button is pressed (e.g., and pause if the button is released). And in some embodiments, the alignment and docking process can be incorporated as an input to manual movement of the robotic arm (e.g., during an admittance mode).

B. ADM and Image Sensor

Figure 26:
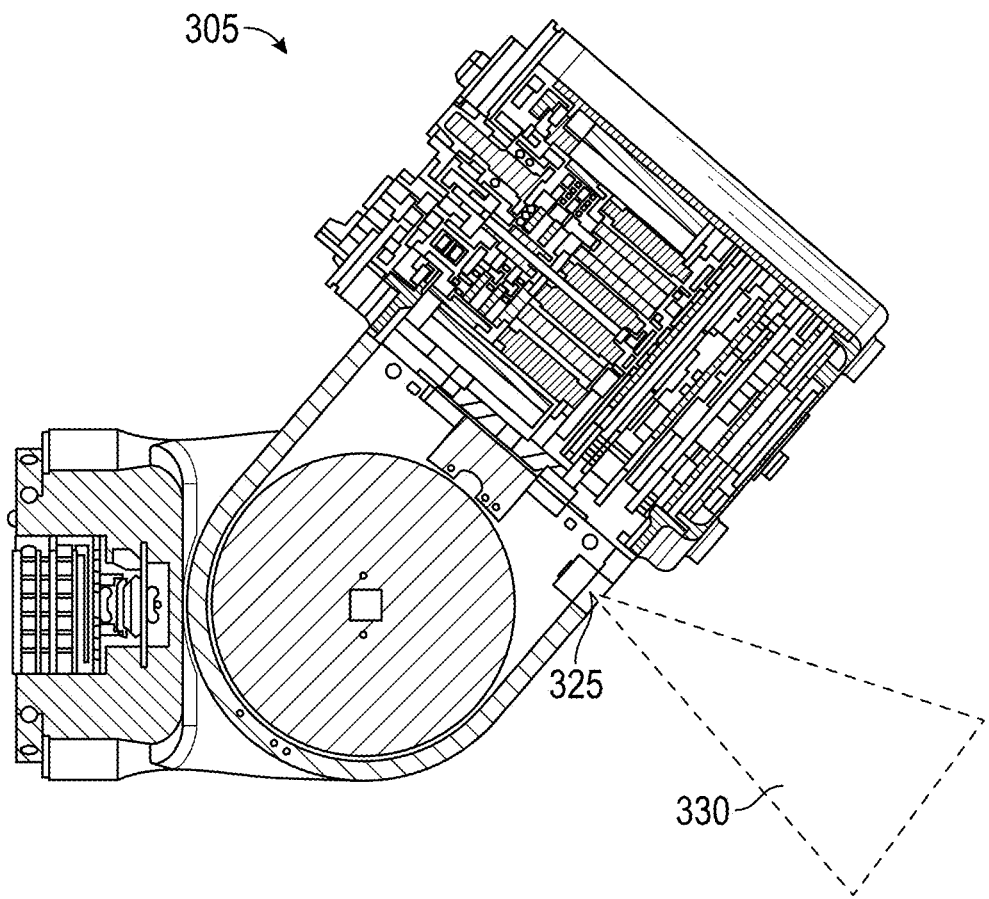
FIG. 26 is an example embodiment of an ADM including an image sensor in accordance with aspects of this disclosure.

FIG. 26 is an example embodiment of an ADM 305 including an image sensor 325 in accordance with aspects of this disclosure. The ADM 305 illustrated in FIG. 26 can be used in the method 270 described in connection with FIG. 22 and/or the system and techniques described in connection with FIGS. 23-25. An image sensor 325 may be installed on a portion of the ADM 305 so as to capture images within a field of view 330. The image sensor 325 may be located such that the field of view 330 includes the remote center of motion (not illustrated) of the ADM 305. In the illustrated embodiment, the image sensor 325 is recessed in the body of the ADM 305. In other embodiments, the image sensor 325 may be attached to an outer surface of the ADM 305.

For certain procedures, a sterile drape (not illustrated) may be coupled to the ADM 305 to provide a barrier between the ADM 305 and the patient. The sterile drape may cover at least a portion of the ADM including the image sensor 325. Since in some instances, the sterile drape may be opaque, the sterile drape may include a transparent region that overlaps with the image sensor 325 such that the image sensor 325 can view the port via the transparent region. Thus, the transparent region may be configured so that the field of view 330 is substantially unobstructed by the sterile drape.

Figure 27:
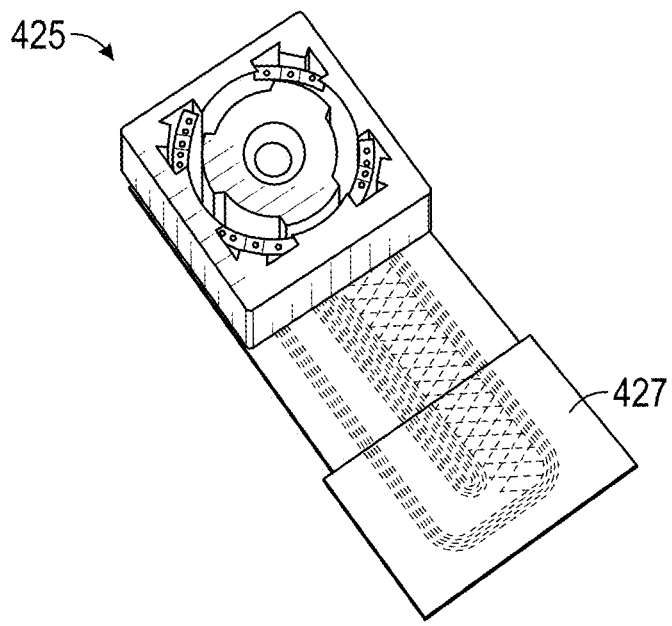
FIG. 27 illustrates an embodiment of an image sensor 425 in accordance with aspects of this disclosure.

FIG. 27 illustrates an embodiment of an image sensor 425 in accordance with aspects of this disclosure. The image sensor 425 is illustrated here prior to attachment to an ADM or other location within the system. The image sensor 425 may include an attachment portion 427 configured to be electrically coupled to a corresponding portion (e.g., a pad or other electrical connector) on the ADM, robotic arm, or other attachment point in the system.

C. Cannula and Fiducial

Figure 28A:
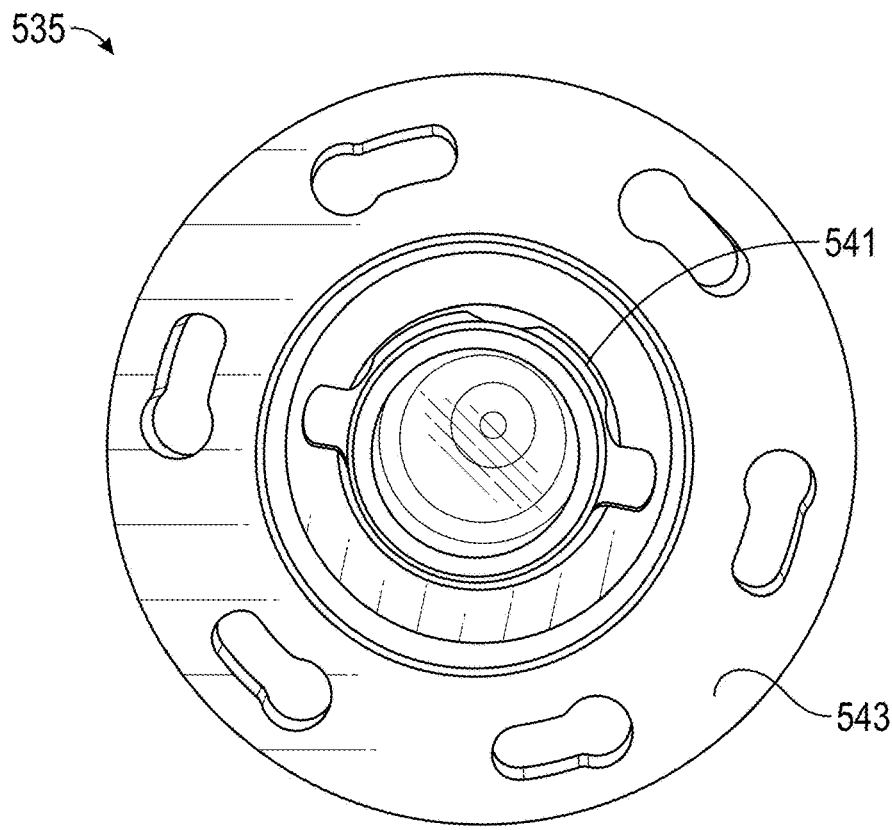
FIG. 28A illustrates an example embodiment of a cannula in accordance with aspects of this disclosure.

In certain implementations, the port can be embodied as a cannula or similar instrument placed into a body wall of the patient. FIG. 28A illustrates an example embodiment of a cannula 535 in accordance with aspects of this disclosure. The cannula 535 of FIG. 28A includes an inner portion 541 and an outer portion 543 on which one or more fiducials (not illustrated) can be placed. When the sensor comprises as an image sensor, the fiducial may include a marking visible and detectible by the image sensor. The fiducial may be located on one or more of the inner and outer portions 541 and 543 of the cannula 535.

Figure 28B:
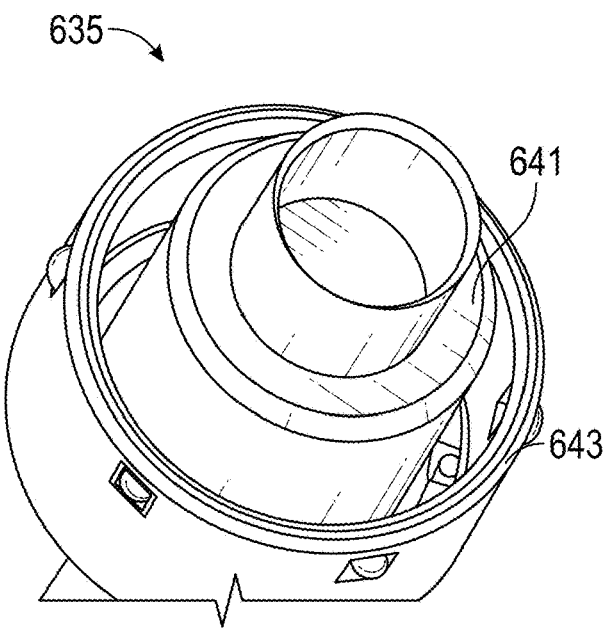
FIG. 28B illustrates another example embodiment of a cannula in accordance with aspects of this disclosure.

FIG. 28B illustrates another example embodiment of a cannula 635 in accordance with aspects of this disclosure. The cannula 635 of FIG. 28B also includes an inner portion 641 and an outer portion 643 on which a fiducial can be placed. Here, the inner portion 641 of the cannula 635 may have a larger surface area than the inner portion 541 of the cannula 535, and vice versa with respect to the outer portions 643 and 543 of the two cannulas 635 and 535, respectively. Thus, in certain embodiments, the fiducial may be more suitable to be placed on the outer cannula 543 of the cannula 535 of FIG. 28A and the inner portion 641 of the cannula 635 of FIG. 28B.

Figure 29:
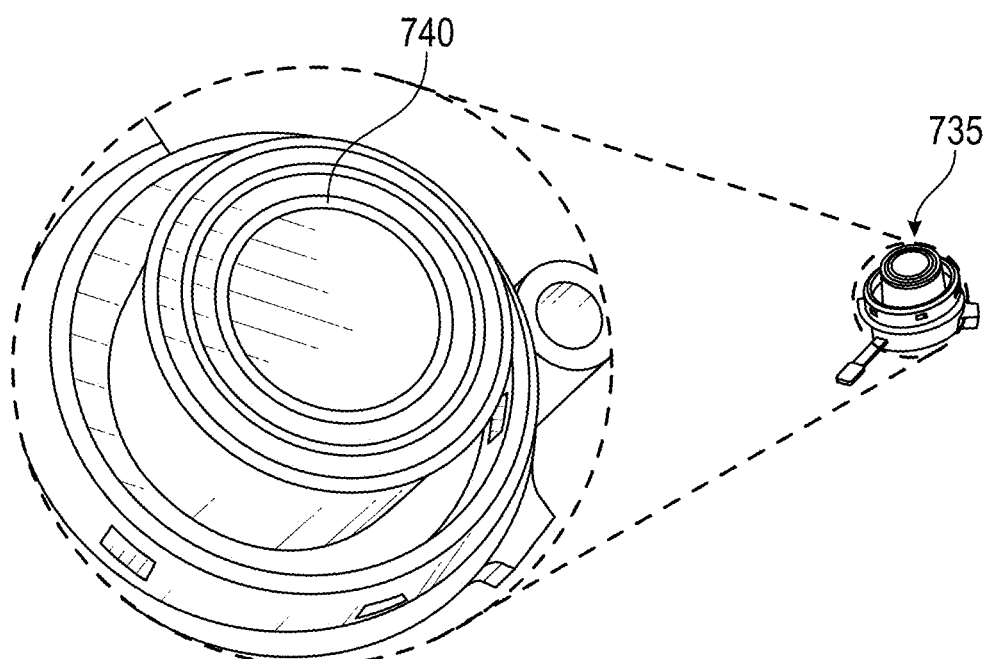
FIG. 29 illustrates an example fiducial formed on a cannula in accordance with aspects of this disclosure.

In some embodiments, the fiducial can be a mark or pattern that is formed on a portion of the cannula 535 or 635. FIG. 29 illustrates an example fiducial formed on a cannula 735 in accordance with aspects of this disclosure. As shown in FIG. 29, the cannula 735 may include a fiducial 740 formed on a surface thereof so as to be visible to an image sensor. The fiducial may include a mark or pattern having contrasting regions that enable the detection of the cannula by the image sensor. In some embodiments, the fiducial can be removably fixed to the cannula, rather than a part of the cannula itself. In some embodiments, as shown in FIG. 29, the fiducial can be in the form of a circle or ring, which can help to simplify the calculation by the processor of the relative distance and orientation between the robotic arm and the cannula as described below. However, the fiducial need not be in the form of a circle or ring, and can be any shape that is detectable by the sensor.

Figure 30:
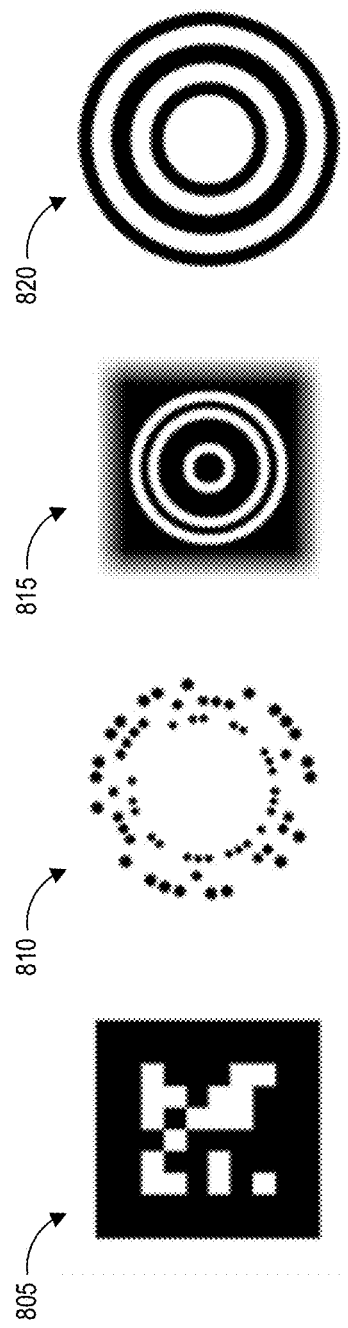
FIGS. 30A-30D illustrate example embodiments of fiducial which can be used in accordance with aspects of this disclosure.

FIGS. 30A-30D illustrate example embodiments of fiducials which can be used in accordance with aspects of this disclosure. For example, one fiducial 805 as illustrated in FIG. 30A may include a high contrast block pattern, similar to a QR code, which may be asymmetrical to provide orientation information of the fiducial. The fiducial 810 illustrated in FIG. 30B may include a high contrast circular pattern which may be asymmetrical to provide orientation information of the fiducial. FIGS. 30C and 30D illustrate fiducials 815 and 820 with high contrast circular rings having different thicknesses that can also be used.

Figure 31:
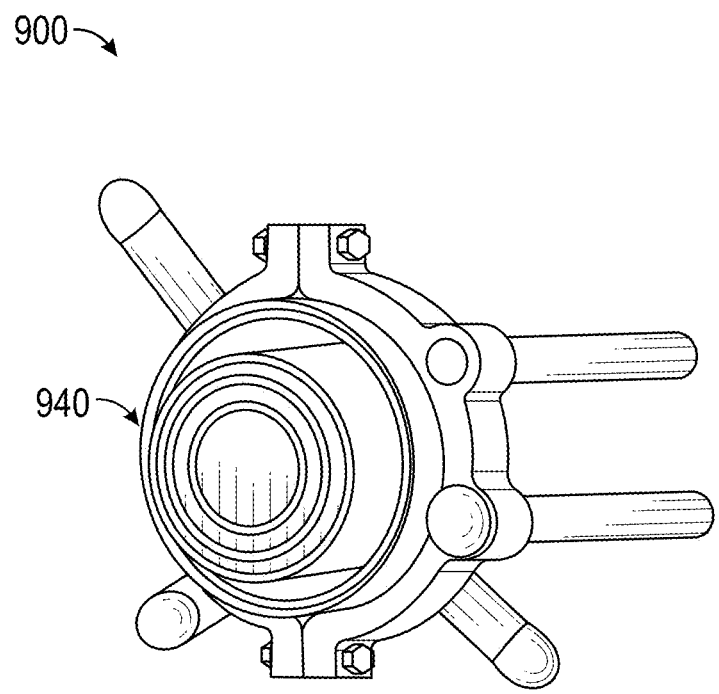
FIG. 31 is an example image of a fiducial captured by an image sensor in accordance with aspects of this disclosure.

FIG. 31 is an example image of a fiducial captured by an image sensor in accordance with aspects of this disclosure. The image 900 includes a fiducial 940 which is located at a certain distance and orientation with respect to the image sensor. The processor may use the size and shape of the fiducial 940 within the image 900 to determine the relative distance between the fiducial 940 and the image sensor. For example, the size of the fiducial 940 within the image 900 may be directly related to the distance between the fiducial 940 and the image sensor.

Figure 32A:
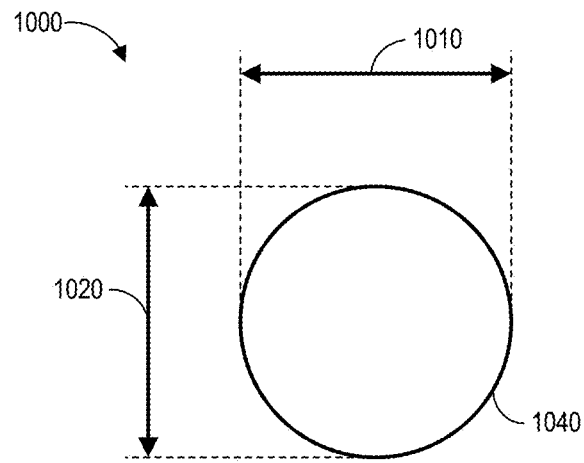
FIGS. 32A and 32B illustrate simplified views of a fiducial captured by an image sensor in accordance with aspects of this disclosure.
Figure 32B:
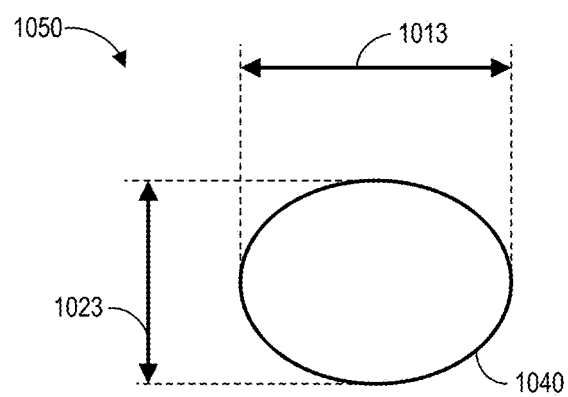

FIGS. 32A and 32B illustrate simplified views of a fiducial captured by an image sensor in accordance with aspects of this disclosure. In the view 1000 of FIG. 32A, the fiducial 1040 may be represented as a circle having the same width 1010 and height 1020. If the fiducial 1040 includes a circular marker, then the image sensor may be aligned with the fiducial 1040 when the fiducial 1040 forms a circle within the image 1040. In the view 1050 of FIG. 32B, the image sensor may not be aligned with the fiducial, and thus, the fiducial 1040 may be represented by an oval rather than a circle. The ratio between the lengths of the major axis 1013 and the minor axis 1023 of the fiducial 1040 may be related to the angle formed between the image sensor and the fiducial. Further, when the fiducial 1040 has the shape of a circle, the major axis of the fiducial within the representation of the fiducial 1040 within the image 1050 may only depend on the distance between the fiducial 1040 and the image sensor.

In view of the above, the processor can determine the angle between the tool path axis and the insertion axis based on the shape of the fiducial 1040 within a field of view of the image sensor. Similarly, the processor can also determine the distance between the image sensor and the fiducial based on the length of the major axis of the fiducial within the field of view of the image sensor. Thus, when the fiducial has the form of a circle or ring, the processor may be able to more easily determine the relative distance and orientation between the image sensor (and thus the ADM) and the port. However, the fiducial need not be in the form of a circle or ring, and can be any shape that is detectable by the image sensor.

D. Ports and Surgical Procedures

The alignment and docking procedures described herein may be applied to a variety of different surgical procedures, some of which may use different types of ports or may involve aligning the ADM to a natural orifice of the patient without the use of a port. In one embodiment, the port may include a patient introducer or sheath placed into a natural orifice of the patient. For example, the patient introducer may be configured to be installed in a mouth or nose of the patient, for example, for use during a bronchoscopy procedure. In another embodiment, a sheath can be configured to be secured to a ureteroscope coupled with the robotic arm. In yet another embodiment, the port can be configured to be placed in the patient's sinus for an otolaryngology (ENT) procedure. In other embodiments, the ADM may be aligned to the patient's sinus for an ENT procedure without the use of a port.

Figure 33:
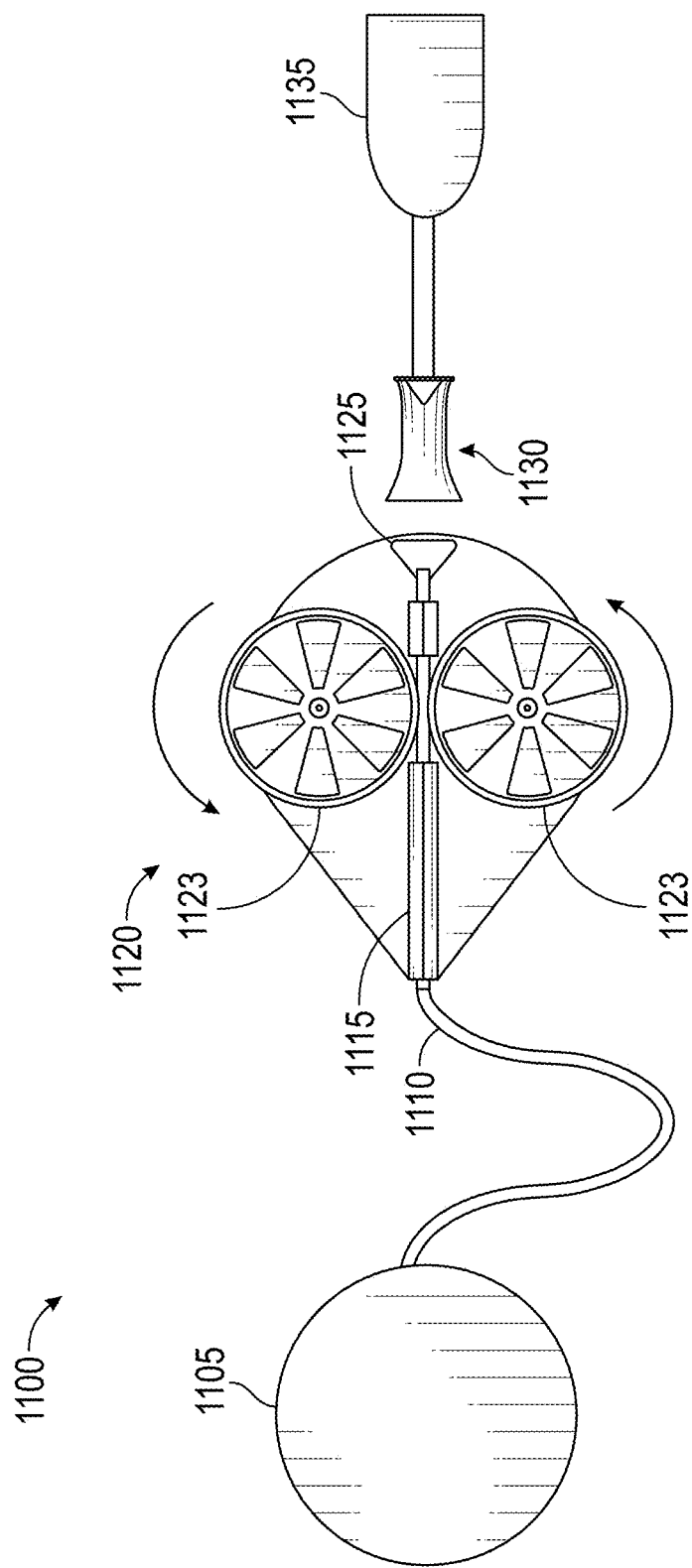
FIG. 33 illustrates an example feed roller system for which the described aligning and docking procedures can be applied.

The alignment and docking procedure may also be applied to procedure using a feed roller configured to receive a scope, e.g., for a ureteroscopic procedure. FIG. 33 illustrates an example feed roller system for which the described aligning and docking procedures can be applied. The system 1100 includes a ureteroscope handle 1105, a ureteroscope shaft 1110 with a service loop, a shaft guide 1115, a feed roller device 1120 including a pair of feed rollers 1123, a renal stone collector 1125, an optional ureteral access sheath 1130, and a patient 1135. The alignment and docking methods disclosed herein can be used to align and/or dock the feed roller device 1120 with the ureteral access sheath 1130 and/or the patient 1135. For example, the feed roller device 1120 can include a sensor (such as an image sensor) configured to determine the relative position of the reed roller device 1120 with respect to the ureteral access sheath 1130 by detecting the location of a fiducial located on or near the ureteral access sheath 1130. The feed roller device 1120 may also be used in other procedures, such as a bronchoscopic procedure and a gastrointestinal (GI) procedure.

3. Implementing Systems and Terminology

Implementations disclosed herein provide systems, methods and apparatus for alignment and docking of a robotic arm are provided.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The alignment and docking functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A method, comprising:
   receiving, from a sensor, information indicative of a position of an instrument driver of a robotic arm with respect to an access point associated with a patient;
   determining, with one or more processors in communication with the sensor, that the instrument driver is at a first position in which a tool path axis associated with the instrument driver is not in alignment with an insertion axis associated with the access point; and
   providing, with the one or more processors, a command to move the instrument driver to a second position in which the tool path axis is in alignment with the insertion axis.

2. The method of claim 1, wherein the access point includes a port installed in the patient.

3. The method of claim 1, wherein the sensor comprises a camera.

4. The method of claim 1, wherein the sensor is attached to the robotic arm.

5. The method of claim 4, wherein the sensor is attached to the instrument driver.

6. The method of claim 1, wherein the sensor is attached to a bed, a cart, or another robotic arm.

7. The method of claim 1, wherein the information received from the sensor includes one or more images of a fiducial associated with the patient.

8. The method of claim 7, wherein the fiducial is attached to a cannula installed in the access point.

9. The method of claim 7, wherein the fiducial is positioned on at least one of the patient or draping in a known spatial relationship with respect to the access point.

10. The method of claim 1, further comprising:
    determining, with the one or more processors, an angle between the tool path axis and the insertion axis, wherein the first position in which the tool path axis is not in alignment with the insertion axis is determined based on the angle.

11. The method of claim 1, further comprising:
    determining, with the one or more processors, a distance between the tool path axis and the insertion axis, wherein the first position in which the tool path axis is not in alignment with the insertion axis is determined based on the distance.

12. A non-transitory computer readable storage medium having stored thereon instructions that, when executed, cause at least one computing device to:
    receive information from a sensor configured to generate information indicative of a location of a port installed in a patient;
    determine that a robotic arm is located at a first position in which a tool path axis associated with the robotic arm is not in alignment with an insertion axis of the port; and
    provide a command to move the robotic arm to a second position in which the tool path axis associated with the robotic arm is in alignment with the insertion axis.

13. The non-transitory computer readable storage medium of claim 12, wherein the sensor comprises an image sensor.

14. The non-transitory computer readable storage medium of claim 13, wherein the port comprises a fiducial.

15. The non-transitory computer readable storage medium of claim 14, further having stored thereon instructions that, when executed, cause the at least one computing device to:
    determine an angle between the tool path axis and the insertion axis based on the fiducial within a field of view of the image sensor.

16. The non-transitory computer readable storage medium of claim 14, further having stored thereon instructions that, when executed, cause the at least one computing device to:

determine a distance between the tool path axis and the insertion axis based on the fiducial within a field of view of the image sensor.

17. A system, comprising:

a robotic arm comprising a series of links and an instrument driver coupled to a distal end of the series of links, the robotic arm being configured to insert or retract a tool along a tool path axis associated with the instrument driver;

a sensor configured to capture information indicative of a spatial relationship between the tool path axis and an insertion axis of an access point associated with a patient; and one or more processors configured to:

determine, based on the information captured by the sensor, that the tool path axis is not in alignment with the insertion axis; and provide a command to move the instrument driver to a position where the tool path axis is aligned with the insertion axis.

18. The system of claim 17, wherein the sensor comprises an image sensor attached to the robotic arm.

19. The system of claim 17, wherein the one or more processors are configured to determine that the tool is not in alignment based on an angle between the tool path axis and the insertion axis.

20. The system of claim 17, wherein the one or more processors are configured to determine that the tool is not in alignment based on a distance between the tool path axis and the insertion axis.

* * * * *